(12) United States Patent
Bajura et al.

(10) Patent No.: US 8,139,846 B2
(45) Date of Patent: Mar. 20, 2012

(54) VERIFICATION OF INTEGRATED CIRCUITS AGAINST MALICIOUS CIRCUIT INSERTIONS AND MODIFICATIONS USING NON-DESTRUCTIVE X-RAY MICROSCOPY

(75) Inventors: Michael A. Bajura, Arlington, VA (US); John N. Damoulakis, Gambrills, MD (US); Younes Boulghassoul, Arlington, VA (US); Michael P. K. Feser, Concord, CA (US); Andrei V. Tkachuk, Concord, CA (US)

(73) Assignees: University of Southern California, Los Angeles, CA (US); Xradia, Concord, CA (US)

( * ) Notice: Subject to any disclaimer, the term of this patent is extended or adjusted under 35 U.S.C. 154(b) by 620 days.

(21) Appl. No.: 12/265,562

(22) Filed: Nov. 5, 2008

(65) Prior Publication Data

US 2011/0002528 A1     Jan. 6, 2011

Related U.S. Application Data

(60) Provisional application No. 60/985,469, filed on Nov. 5, 2007.

(51) Int. Cl.
*G06K 9/62* (2006.01)
(52) U.S. Cl. .......................... 382/145; 382/131; 382/141
(58) Field of Classification Search .................. 382/145, 382/100, 131, 141, 255; 716/1, 5, 11, 119; 702/65, 155; 250/492.2, 458.1; 378/43, 378/84
See application file for complete search history.

(56) References Cited

U.S. PATENT DOCUMENTS

| 5,177,774 | A  | * | 1/1993  | Suckewer et al. | ............... 378/43 |
| 5,760,901 | A  | * | 6/1998  | Hill            | ............... 356/450 |
| 5,952,668 | A  | * | 9/1999  | Baer            | ............... 250/492.2 |
| 7,454,300 | B2 | * | 11/2008 | Suaya et al.    | ............... 702/65 |
| 7,783,994 | B2 | * | 8/2010  | Ball et al.     | ............... 716/119 |
| 2009/0100392 | A1 | * | 4/2009 | Ivaldi       | ............... 716/5 |

OTHER PUBLICATIONS

Born M. et al. 1999. Principles of Optics. NY: Cambridge University Press: pp. 217-227.
Chao W. et al. 2005. Soft X-ray Microscopy at a Spatial Resolution Better Than 15 nm. Nature, vol. 435: pp. 1210-1213.
Cole, E.I. 2004. Beam-Based Defect Localization Methods. In Microelectronics Failure Analysis/ Desk Reference Fifth Edition. 2004. Ohio: ASM International, Jan. 2004: pp. 406-416.
Hooghan, K. 2004 Focused Ion Beam (FIB) Systems: A Brief Overview. In Microelectronics Failure Analysis/ Desk Reference Fifth Edition. 2004. Ohio: ASM International, Jan. 2004: pp. 583-594.

(Continued)

*Primary Examiner* — Sang Nguyen
(74) *Attorney, Agent, or Firm* — McDermott Will & Emery LLP

(57) ABSTRACT

A method and system for verifying the integrity of integrated circuits (ICs) by detecting the presence of unauthorized circuit insertions or modifications using non-destructive x-ray microscopy is disclosed. A reference image based on a trusted IC or a trusted design file may be generated. An un-trusted IC may be received from an un-trusted foundry, which IC is manufactured in response to the trusted design file provided to the foundry. An x-ray microscope may record a plurality of sets of base images of the un-trusted IC, each set corresponding to a different viewing angle. One or more un-trusted images may be produced from the base images. The reference images may be compared with the un-trusted images to illuminate any additions or modifications in circuit elements or other parameters.

23 Claims, 16 Drawing Sheets

OTHER PUBLICATIONS

Johansson G.A. et al. 2002. Design and Performance of Laser-Plasma-Based Compact Soft X-ray Microscope. Rev. Sci. Instrum, vol. 73: pp. 1193-1197.

Kim K.W. et al. 2006. Compact Soft X-ray Transmission Microscopy with Sub-50 nm Spatial Resolution. Phys. Mol. Biol., vol. 51: pp. N99-N107.

McDonald, J. 2004. Optical Microscopy. In Microelectronics Failure Analysis/ Desk Reference Fifth Edition. 2004. Ohio: ASM International, Jan. 2004: pp. 540-558.

Microelectronics Failure Analysis. 2004. Desk Reference, Fifth Edition. Edited by The Electronic Device Failure Analysis Society Desk Reference Committee, published by ASM International, Materials Park, Ohio.

Neuhausler U. et al. 2003. X-ray Microscopy in Zernike Phase Contrast Mode at 4 keV Photon Energy with 60 nm Resolution. J. Phys. D. Appl. Phys., vol. 36: pp. A-79-A-82.

Phase Contrast Microscopy. 2000. http://www.microscopyu.com/articles/phasecontrast/phasemicroscopy.html. Downloaded Feb. 26, 2010.

Rudolph D. et al. 1990. Amplitude and phase contrast in x-ray microscopy. Modern Microscopies, New York, Plenum, pp. 59-67.

Schneider G. 1998. Cryo X-ray Microscopy with High Spatial Resolution in Amplitude and Phase Contraast. Ultramicroscopy, vol. 75: pp. 85-104.

Shade, G. 2004. Photon Emission Microscopy. In Microelectronics Failure Analysis/ Desk Reference Fifth Edition. 2004. Ohio: ASM International, Jan. 2004: pp. 347-355.

Subramanian, S. et al. 2004. Transmission Electron Microscopy for Failure Analysis of Integrated Circuits. In Microelectronics Failure Analysis/ Desk Reference Fifth Edition. 2004. Ohio: ASM International, Jan. 2004: pp. 595-614.

Suzuki Y. et al. 2003. Hard X-ray Microscopy Activities at Spring-8. Journal De Physique, vol. 104: pp. 35-40.

Tkachuk A. et al. 2006. High-resolution x-ray tomography using laboratory sources. Developments in X-Ray Tomography V, San Diego, CA, SPIE 2006 Proceedings, 6318, 63181D; doi:10.1117/12.682383. Online publication date: Sep. 7, 2006; Conference Date: Aug. 15, 2006, pp. 63181D-1 to 63181D-8.

Vanderlinde, W. 2004. Scanning Electron Microscopy. In Microelectronics Failure Analysis/ Desk Reference Fifth Edition. 2004. Ohio: ASM International, Jan. 2004: pp. 559-573.

Vanderlinde, W. 2004. Ultra-high Resolution in the Scanning Electron Microscope. In Microelectronics Failure Analysis/ Desk Reference Fifth Edition. 2004. Ohio: ASM International, Jan. 2004: pp. 574-582.

Wang, S. et al. 2002. A Transmission X-ray Microscopy (TXM) for Nondestructive 3D Imaging of IC's at Sub 100-nm Resolution. Proceedings of 28th ISTFA Conference, Phoenix, AZ, pp. 227-233.

Wang, S. 2004. Die Level Fault Localization with X-ray Microscopy. In Microelectronics Failure Analysis/ Desk Reference Fifth Edition. 2004. Ohio: ASM International, Jan. 2004: pp. 253-259.

Wills, K.S. et al. 2004 Delayering Techniques: Dry Processes, Wet Chemical Processing and Parallel Lapping. In Microelectronics Failure Analysis/ Desk Reference Fifth Edition. 2004. Ohio: ASM International, Jan. 2004: pp. 444-465.

Young, M. 1972. Zone plates and their aberrations. Journal of the Optical Society of America, vol. 62, No. 8: pp. 972-976.

Zschech E. et al. 2008. High-resolution X-ray Imaging—A Powerful Nondestructive Technique for Applications in Semiconductor Industry. Applied Physics A: Materials Science & Processing, vol. 92: pp. 423-429.

* cited by examiner

VERIFICATION OF INTEGRATED CIRCUITS AGAINST MALICIOUS CIRCUIT INSERTIONS AND MODIFICATIONS USING NON-DESTRUCTIVE X-RAY MICROSCOPY

CROSS-REFERENCE TO RELATED APPLICATION(S)

This application is based upon and claims priority to U.S. Provisional Patent Application Ser. No. 60/985,469, entitled "Verifying 'Trust' In Integrated Circuits Against Malicious Circuit Insertions And Modifications Using Non-Destructive X-Ray Microscopy", filed Nov. 5, 2007, the entire content of which is incorporated herein by reference.

STATEMENT REGARDING FEDERALLY SPONSORED RESEARCH

This work was made with government support under Grant No. "ERGON" P.O. C06-066454, awarded by the Defense Advance Research Projects Agency (via CACI). The government has certain rights in the invention.

BACKGROUND

1. Field

This application relates to integrated circuit verification.

2. Description of Related Art

An important goal for high-performance electronics used in many sensitive systems, such as systems used for national defense, surveillance, cryptography, banking, the stock market, and many other applications, is to ensure a trusted supply of high performance integrated circuits (ICs) in spite of the fact that many leading-edge integrated circuit foundries and supply chains operate in un-trusted environments. As an example, the microelectronics industry, supplier of hardware capability that underlies much of America's modern commercial and military technology, has outsourced many of its critical microelectronics manufacturing capabilities from the United States to countries with lower-cost capital and operating environments. Trustworthiness and supply assurance for components used in many such commercial and military applications are natural casualties of this outsourcing process. Similarly trust in domestic supplies can also be a concern unless steps have been taken to secure these resources.

Trustworthiness can be a particular concern. This concern may be examined by an analogous example of a computer virus. When a user of a personal computer runs a version of a program that, for example, was obtained from an unknown website, there exists the possibility that the program may contain a software virus which may infect the user's computer. A malicious virus may cause various negative effects, such the slowing down of the computer, damage to other programs, hard drive errors, system crashes, the erasure of data, and the like. To help combat such problems and to help identify the virus before it can cause its damage, the user may run one of the many sophisticated antivirus programs on its computer. The antivirus software may act as a mechanism to verify the integrity of programs run on the user's computer, to thereby sift out such dangerous programs.

An analogous scenario can occur in hardware when an IC supplier or other hardware supplier relies on an un-trusted manufacturer. Because un-trusted fabrication plants and/or supply chains are not under the hardware supplier's control, there is a possibility that "Trojan horses" or other unauthorized design modifications may be inserted into ICs used in commercial and military applications. In addition, more subtle shifts in process parameters or layout line spacing of the ICs could be made which could drastically shorten the lives of components.

Currently, no equivalent of an "antivirus program" exists to identify these hardware changes to the fabricated ICs. Neither post-fabrication electrical testing nor currently available reverse engineering or inspection methods for modern ICs are capable of reliably detecting compromised microelectronic components. By way of an example, an IC may have been manufactured with an unauthorized inclusion of a special circuit that enables the IC to behave in a certain way (e.g., to cause the device to fail, or to activate another device, etc.) only when a specific code is inserted. The IC supplier may test the manufactured IC electrically and determine that the IC performs correctly as per the specifications originally defined by the supplier. Without knowing the specific code, however, the IC supplier cannot determine that an unauthorized circuit has been included in the design.

Current visual and reverse engineering inspection techniques are likewise inadequate. Transistors in IC chips currently have form factors in the tens of nanometers or less, with up to billions of transistors per chip for typical processors. The use of simple magnification methods to view the chip are inadequate due to, among other problems, the typically large number of layers of semiconductor material. One approach to inspection is to combine a physical de-layering process such as focused ion beam (FIB)/reactive ion etching or chemical-mechanical polishing (CMP) with scanning electron microscope imaging as the layers are removed. Unfortunately this process is destructive and can be long and highly labor intensive.

Even if physical de-layering techniques are not used, current x-ray microscopy methods have been deemed by practitioners in the art to be unsuitable for device verification. The common perception among these practitioners is that the use of x-rays has a tendency to damage semiconductors. Therefore, it is not widely viewed as a viable alternative to microelectronics verification.

For an entity such as the government or a computer supplier with a need for trusted electronics components, the currently-available alternative to establish a trusted supply of electronics is to build capability internally in the form of dedicated semiconductor manufacturing capacity. While this alternative has been viable historically, it is becoming cost-prohibitive. To stay on the current edge of technology, manufacturing capacity must be refreshed every couple years. In addition the cost of each new manufacturing plant continues to rise and is currently around four billion dollars per facility. This expense is a concern for both the government and most companies.

What is needed is a novel technique for verification of integrated circuits against malicious circuit insertions and modifications which overcomes the above deficiencies.

BRIEF SUMMARY

Methods for verifying the integrity of ICs against malicious or inadvertent circuit insertions and modifications are disclosed. The ICs may be procured from un-trusted commercial or foreign sources. The ICs may be verified through a two-pronged process of electrical testing and inspection using x-ray microscopy, at much lower overall cost. In addition, circuit design practices coupled with electrical testing may be employed in custom-designed ICs to better-facilitate x-ray inspection for additional levels of security.

A system for verifying the integrity of integrated circuits (ICs) procured from an un-trusted source may include an x-ray imaging device, and a processing system configured to cause the x-ray imaging device to generate one or more base images of an un-trusted IC, produce at least one un-trusted image using the one or more base images, the at least one un-trusted image comprising a plurality of connected components from the un-trusted IC, compare the at least one un-trusted image with at least one reference image comprising a plurality of connected elements from a trusted source, and identify one or more differences in the connected elements between the un-trusted image and the reference image.

A method for verifying the integrity of integrated circuits (ICs) procured from an un-trusted source by detecting unauthorized circuit insertions or modifications, including generating, from an x-ray microscope, one or more base images of an un-trusted IC, producing at least one un-trusted image using the one or more base images, the at least one un-trusted image comprising a plurality of connected elements from the un-trusted IC, comparing the at least one un-trusted image with at least one reference image comprising a plurality of connected elements from a trusted source; and identifying one or more differences in the connected elements between the un-trusted image and the reference image.

A system for verifying the integrity of integrated circuits (ICs) procured from an un-trusted source including x-ray microscope means for generating base images of an un-trusted IC, stitching means for producing un-trusted images using the base images, the un-trusted images comprising a plurality of connected elements from the un-trusted IC, comparison means for comparing the un-trusted images with a reference image comprising a plurality of connected elements from a trusted source, and determining means for identifying differences in the connected elements between the un-trusted images and the reference images.

In one aspect, the x-ray imaging device is an x-ray microscope.

In another aspect, a synchrotron is used as the x-ray source.

In another aspect, an annealing step is applied to ICs exposed to the x-ray microscopy to reduce the adverse effects of radiation.

These, as well as other objects, components, steps, features, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

Figure 1:
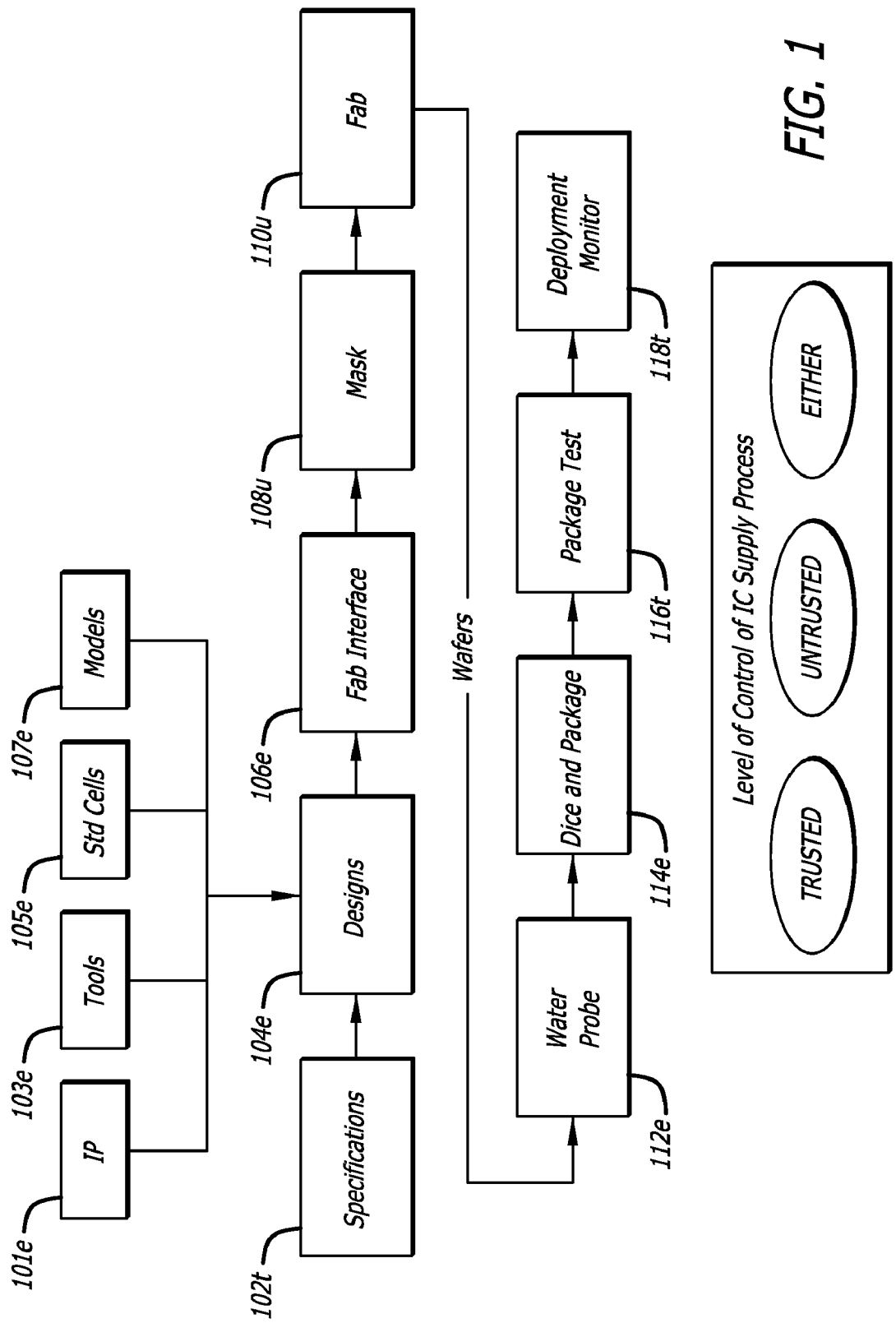
FIG. 1 illustrates a block diagram of an exemplary semiconductor supply chain which gives rise to certain vulnerabilities in semiconductor fabrication addressed by the present disclosure.

The evolving trend toward un-trusted, or offshore, fabrication has reduced the opportunity to control the process of semiconductor production, and rendered various process steps vulnerable to manipulation by an adversary. FIG. 1 shows one illustration of an typical semiconductor supply chain giving rise to these vulnerabilities. A hardware supplier defining a set of specifications for a particular IC may comprise a trusted process 102$t$. The specifications result in a circuit design, which may include a computer aided design software suite of tools 103$e$, standard cell libraries 105$e$ and other circuit and wiring models 107$e$. The "e" signifies that these sources may be either trusted or un-trusted. The circuit design results in a layout or blueprint which is submitted to the semiconductor foundry abroad in a format that meets the specifications of the foundry. These steps include design 104$e$ and fab interface 106$e$.

These processes are denoted "e" rather than "t" because a close coupling may exist between fabrication and design. As IC fabrication moves offshore or into un-trusted environments, the design and tools used for design are increasingly un-trusted as well. As this occurs, many opportunities arise for the introduction of unwanted features into the IC during the design cycle. The design tools may alter or render invalid the functional test vectors used during packaged IC tests. In addition, the intellectual property (IP) used in IC designs may be developed and designed offshore, and traditional design tool vendors are performing an increasing amount of development work offshore.

Figure 2:
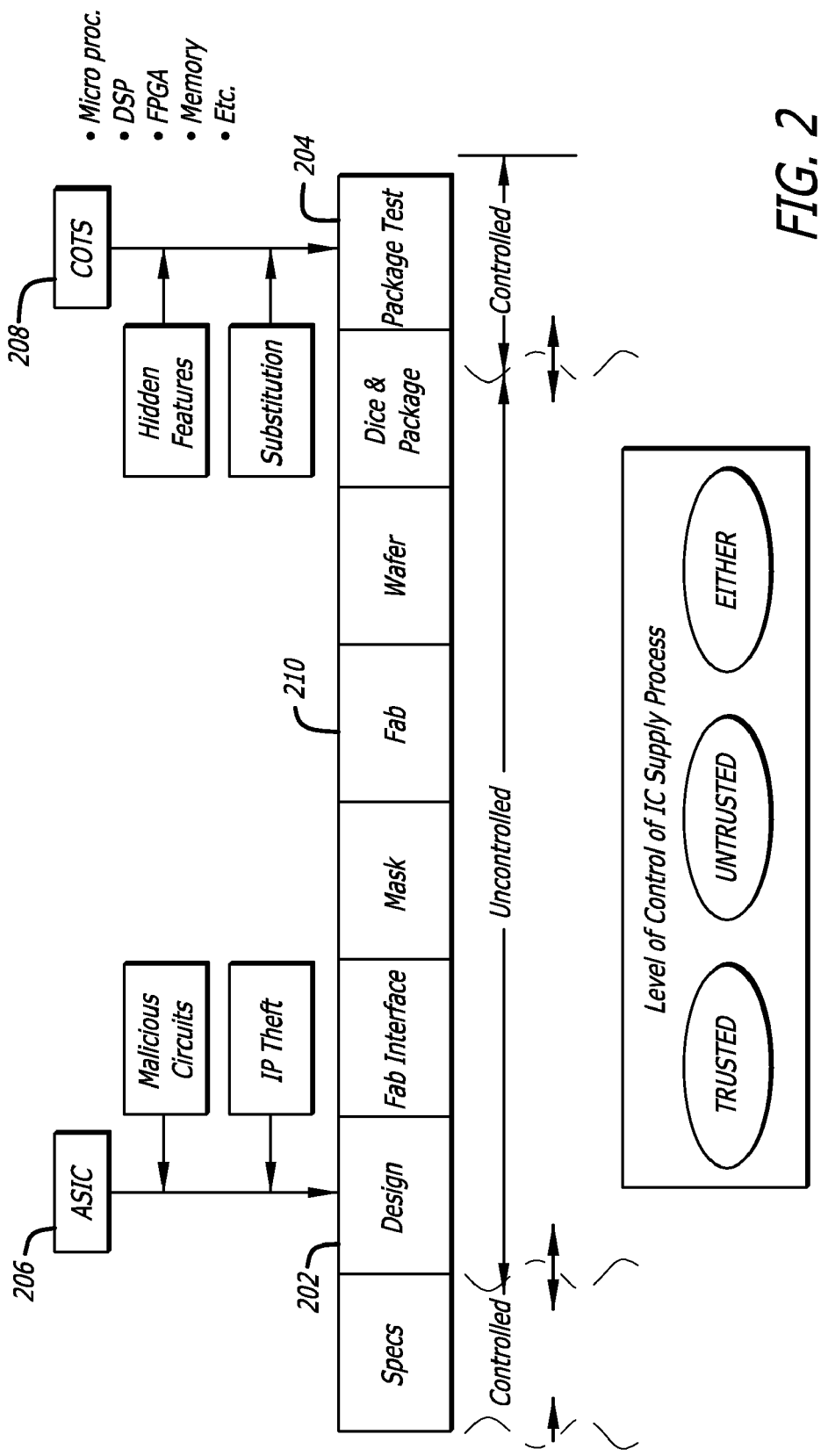
FIG. 2 illustrates a block diagram of an exemplary semiconductor supply chain process in which ASICs and configurable semiconductor vulnerabilities are compared.

Verification issues for ASIC designs may differ in some embodiments from issues associated with commercial configurable hardware designs. Referring to FIG. 2, ASIC 206 and commercially configurable parts (COTS) 208 may take different paths through the supply chain process. Commercially-configurable parts may include, for example, programmable microprocessors, DSPs, FPGAs, memory chips, etc. ASIC product consumers may in some instances have more control over the design process 202 of ASICs, but vulnerabilities may arise from un-trusted design tools and a lack of control during the fabrication process 210. The manufacture of ASIC parts, however, may provide more control over the wafer probing and packaging options.

Commercial configurable parts 208 may also have hidden or private features that can be exploited and remain undetected through package test 204, including, for example, malicious configuration and firmware reprogramming. In addition, the integrity of these parts may be corrupted if a counterfeit commercial configurable part (which may contain intentional or inadvertent manipulated functionality) is inserted into the supply chain.

Hardware Validation Using X-Ray Microscopy

Accordingly, disclosed herein is a hardware validation technique based on x-ray microscopy to ensure trust in the manufacture and distribution of ICs by verifying that they are unaltered from their original designs. In one aspect, an X-ray inspection technique may detect IC wire modifications with high accuracy including all standard-cell-level modifications to a design. As used herein, the X-ray imaging is non-destructive, and any damage may be repaired through an annealing process. The technique can be used to compare ICs with each other, or with a reference design to jump-start inspection of a batch of un-trusted ICs.

As noted above, a physical inspection is needed to find un-testable hardware changes or additions to an IC, whether those changes or additions were inadvertent, malicious, or simply a result of a defective fabrication. According to an aspect, x-ray microscopy is used to perform the inspection. The understanding held by practitioners in the art that x-ray exposure is prohibitively damaging to ICs originates from the primary mechanism of unwanted positive charges retained by IC devices having form factors greater than 90 nm, after those devices are subjected to x-rays. The inventors have discovered, however, that IC devices having form factors of 90 nm and less (and hence smaller gate sizes, etc.), which account for the majority of ICs being newly developed, are much less likely to retain this positive charge. Thus, modern ICs are much less likely to be damaged by x-ray bombardment. Further, any such damage that may occur as a result of an IC's exposure to x-rays may be repaired according to another aspect by an annealing step. In short, the x-ray microscopic techniques disclosed herein have the resolution and penetration to detect wiring on every transistor non-destructively.

Figure 3:
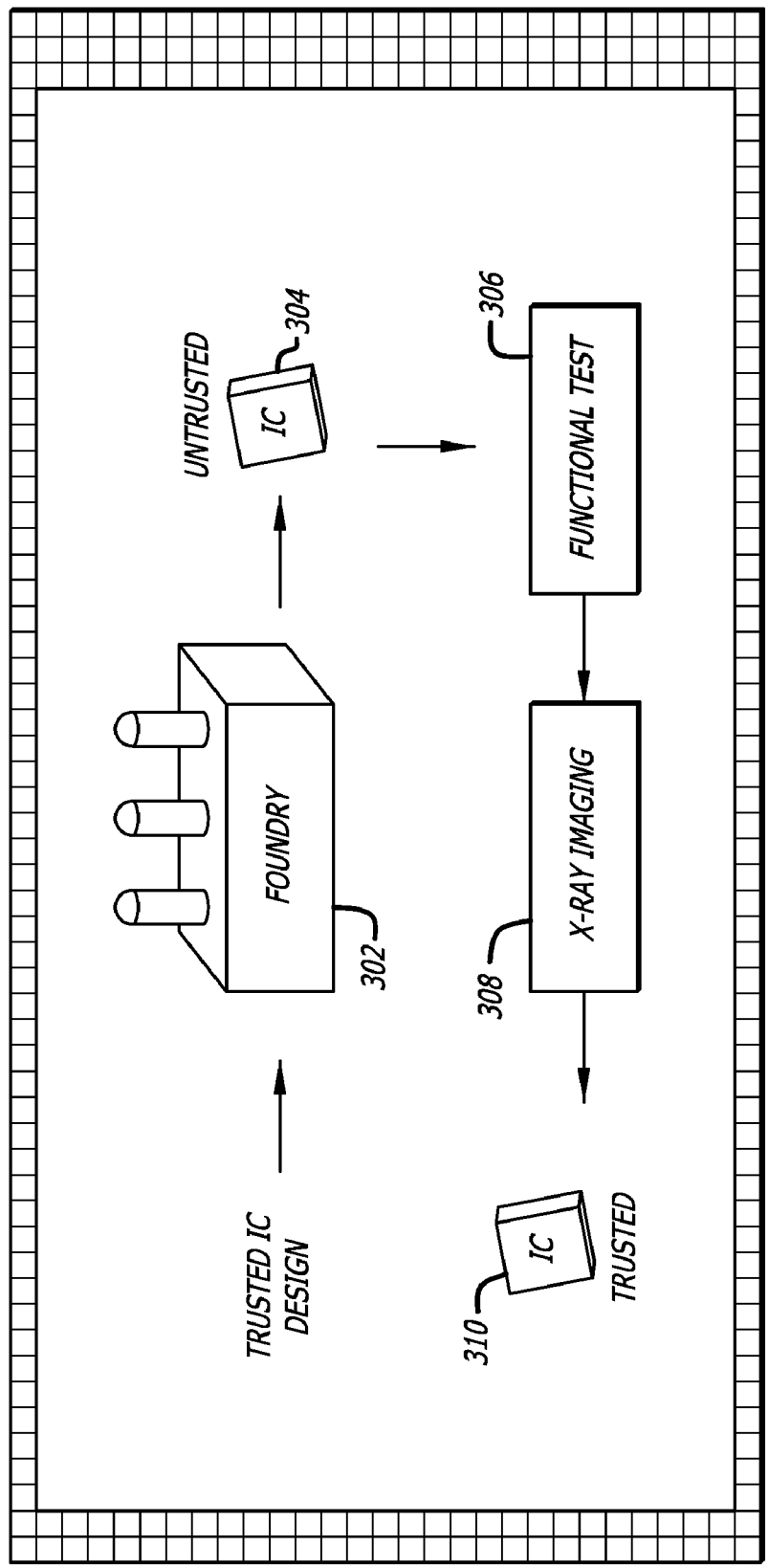
FIG. 3 illustrates an exemplary flow diagram of a method for IC validation according to the present disclosure.

FIG. 3 illustrates a basic flow diagram of an embodiment of the overall process for IC design verification. A trusted IC design from a domestic hardware supplier is provided to an un-trusted foundry 302, perhaps located abroad. The foundry 302 fabricates the un-trusted IC 304. The fabricated ICs 304 are returned to the hardware supplier, whereupon functional testing 306 is performed to verify that the ICs operate according to specification and within design parameters. Thereupon, the hardware and structure of the ICs are validated using the x-ray imaging technique 308 as disclosed herein, to produce a lot of trusted ICs 310. During x-ray imaging 308, according to a preferred embodiment, wiring on every transistor on every IC is inspected against an original trusted design. The trusted ICs 310 may be deployed in sensitive (e.g., military or commercial mission-critical) applications. Annealing may be used to repair any radiation damage caused by the x-ray imaging step 308. In one embodiment, a synchrotron or other bright source is used as a source of x-rays for timely imaging. In general, the above combination of steps 306 and 308—i.e., the combination of functional testing and imaging of metal interconnect and/or gates—may tightly constrain the possible design additions or modifications that can be made by an un-trusted source.

Although basic x-ray inspection of an IC cannot image transistors directly, it is extremely effective in detecting modifications to an IC. When combined with a partitioning design technique which can be inspected with x-rays, even the types of modifications which are not visible to x-rays can be detected through functional tests.

The ability to analyze ICs with x-ray techniques as disclosed herein represents a significant advancement in reverse-engineering capabilities, and is a superior method for helping determine the functionality of any new circuitry discovered in an IC.

Inadequacy of Functional Testing Alone

Although functional testing can help ensure that un-trusted ICs contain expected circuitry, functional testing cannot reliably detect the presence of additional, possibly malicious circuitry. Unless the complexity of an unknown circuit added to an IC design can be bounded, it is not possible to exhaustively enumerate all the functional tests needed to exclude the presence of that unknown circuit.

X-ray imaging may be necessary to ensure trust in IC manufacturing is because it is theoretically impossible to enumerate all the possible trigger states needed to activate and therefore detect an arbitrary unknown "Trojan horse" circuit using functional testing alone. If the state space of possible triggers can be limited, then it is theoretically possible to enumerate all the possible trigger states of an unknown circuit, even though the state space may be quite large. This result falls naturally out of basic computing theory. As an example, consider an embedded state machine which is triggered by a specific numerical sequence. If the trigger sequence is a 128-bit quantity it would take $10^{22}$ years to enumerate all the possible states at 1 GHz. If external inspection can limit the possible trigger sequence to a 32-bit quantity instead, at 1 GHz it would take 4 seconds to guess all the possible triggers, making it practical to test for possible triggers.

Thus, in another aspect, a two-pronged hybrid IC inspection is proposed. In a first prong, standard IC design and functional testing methodologies may be used to ensure devices both contain their expected circuits and do not contain predicted possible manufacturing defects (e.g., nearby shorts or parasitic transistors, etc.). In a second prong, x-ray inspection of metal structures may be used to ensure devices do not contain new circuits and that the expected circuits have not been modified from their original design.

In an aspect, the technique according to the disclosure includes approaches for detecting both first and second order IC modifications and additions. These are discussed below.

Detecting First-Order Ic Modifications

In another aspect, x-ray microscopy is used to detect first-order IC modifications. X-ray microscopy currently has the resolution to directly inspect every wire in an IC at the transistor level. Detecting wiring changes alone is very effective. First order modifications include, for example, ones which add or remove transistors, including all "standard-cell level" modifications to a design. Generally, all metal changes will be visible from x-ray images. In addition, it is difficult for an adversary to add significant logic to produce a circuit capable of a complex attack (e.g., a circuit that can subsequently "take over" a computer in which it resides and transmit data from the computer) by merely changing the invisible diffusion and polysilicon layers only. This is because it the cascading of transistors cannot be easily accomplished without the metal interconnect. Further, existing metal interconnects cannot be reused while preserving the functionality expected by functional testing. Moreover, significant changes to diffusion or polysilicon may degrade at-speed performance of the IC, an event which may be detected during the first prong (functional test).

ICs may first be inspected in a verification flow using x-rays to determine that their wiring matches that of either a trusted reference design file, or a reference "gold standard" IC. The term "gold standard" as referred to herein means the presence of a reserved reference item of a known, trusted design or a manufactured part that can be used to assess the trust of the item in question. Next, standard functional tests may be applied to ensure all the expected functionality in an IC is present as described above. Although x-ray imaging may be nearly insensitive to the polysilicon and diffusion layers that define transistors in an IC, the combination of constraints created by detecting wiring differences and performing standard functional tests may be highly effective in detecting obvious or significant modifications to an IC's design. It is difficult or impossible to add a single standard gate to an IC design without adding wiring and being detected by x-ray imaging.

If additional transistors are created that do not involve adding wiring, their functionality is limited because they must share wiring nodes with existing metal structures, which is likely to cause failures during functional testing. While many transistors or "gates" can be created in invisible polysilicon and diffusion layers, they cannot be cascaded because doing so would require a metal contact between a diffusion layer and a polysilicon layer which would be detected in X-ray images. Accordingly, detecting simple wiring modifications may be used to detect obvious or significant changes to an IC's design.

Detecting Second-Order Ic Modifications

Figure 15:
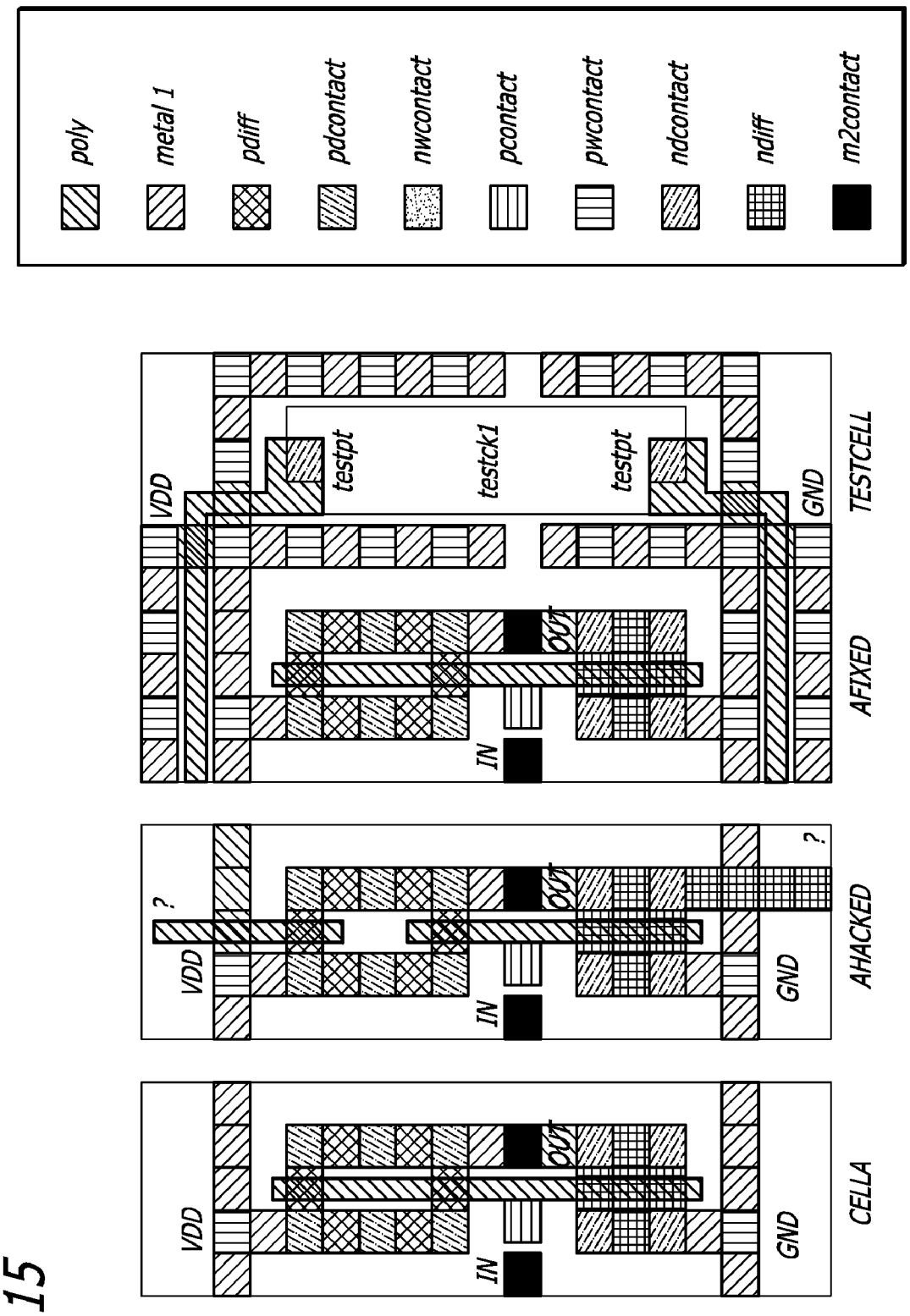
FIG. 15 illustrates an integrated circuit structure having an unauthorized circuit modification.
Figure 16:
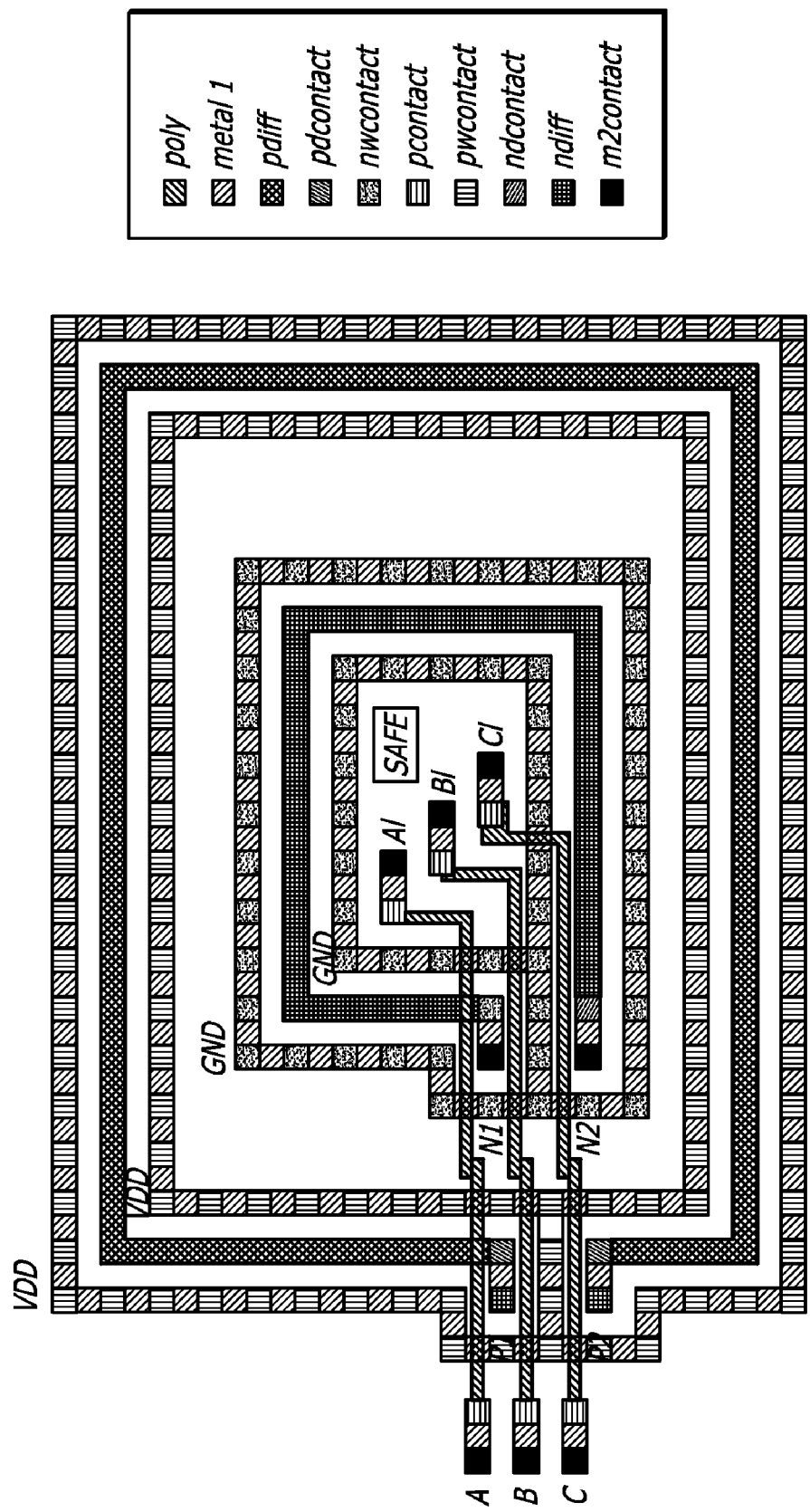
FIG. 16 illustrates an exemplary design concept for a barrier test circuit of an integrated circuit structure which may be used to partition blocks of standard cells.

In another aspect involving ASICs where area and cell partitioning structures can be added during an IC's trusted design phase, additional assurances can be made beyond the first-order tests described above. Partitioning structures may limit the scope of modifications which can be added and escape X-ray detection making it is possible to enumerate the types of modifications which could have been made in a particular design. These modifications can then be effectively probed using functional testing methods. Thus, after detecting wiring changes using x-ray microscopy, the process of detecting unauthorized or inadvertent diffusion or polysilicon changes with test circuits and/or design practices may be used as a basis of defense against second order alterations. Toward removing the last bit of uncertainly out of the inspection process, testing must be performed to rule out the presence of any residual transistor circuits which escape the first set of tests. Unless the candidate set of possible circuits can be limited, it is in general not possible to enumerate the types of circuits which "might" be there by functional testing. It is possible, however to create structures and test circuits which can partition a design into smaller sub-sections where the types of possible modifications can be enumerated, making a fully-complete testing approach. An example of the types of modifications which can escape x-ray inspection is shown in FIG. 15. Here a simple inverter cell, CELL A, is hijacked by changing the diffusion layers and bringing in signals from outside the cell on both the top and bottom sides (A HIJACKED). The (A FIXED) version of the inverter cell uses metal contacts connected to both power and ground rails to limit the intrusion of diffusion into the cell; while a test-structure around the perimeter prevents poly from "sneaking in". FIG. 16 illustrates the design concept for a barrier test circuit which could be used to partition blocks of standard cells to make the functional testing by enumeration hypothesis valid. Constraints placed by passing electrical tests between test points ensure that two diffusion barriers are in place, and that any remaining routing channels into or out of the barrier structure on poly are already filled.

X-Ray Imaging

X-rays have the resolving power (i.e. small enough wavelength) to resolve the finest metal structures in ICs, such as level one metal and substrate contacts, in current and future IC technologies. X-ray microscopy resolution has been demonstrated to a few tens of nanometers, which is smaller than the anticipated dimensions of wiring structures through the 32 nm design node.

Combined with an annealing step, modern ICs can tolerate the irradiation needed for x-ray inspection without permanent effects. Recent data has shown that devices manufactured in IBM's 9LP (90 nm low-power CMOS) process could be irradiated with up to 2 Mrads and have a complete recovery-_after a two day annealing step in a simple oven. The nature of the damage and recovery suggests that these devices could tolerate significantly higher does and still be undamaged. Other measurements and calculations indicate that the irradiation levels needed for IC inspection are well within this range, requiring a maximum of 3 Mrads of surface irradiation (reduced to less than half this when the depth attenuation to sensitive structures is considered) for a full 3D inspection of an IC at a resolution of 50 nm.

Image Processing and Flow for Ic Inspection

Figure 4:
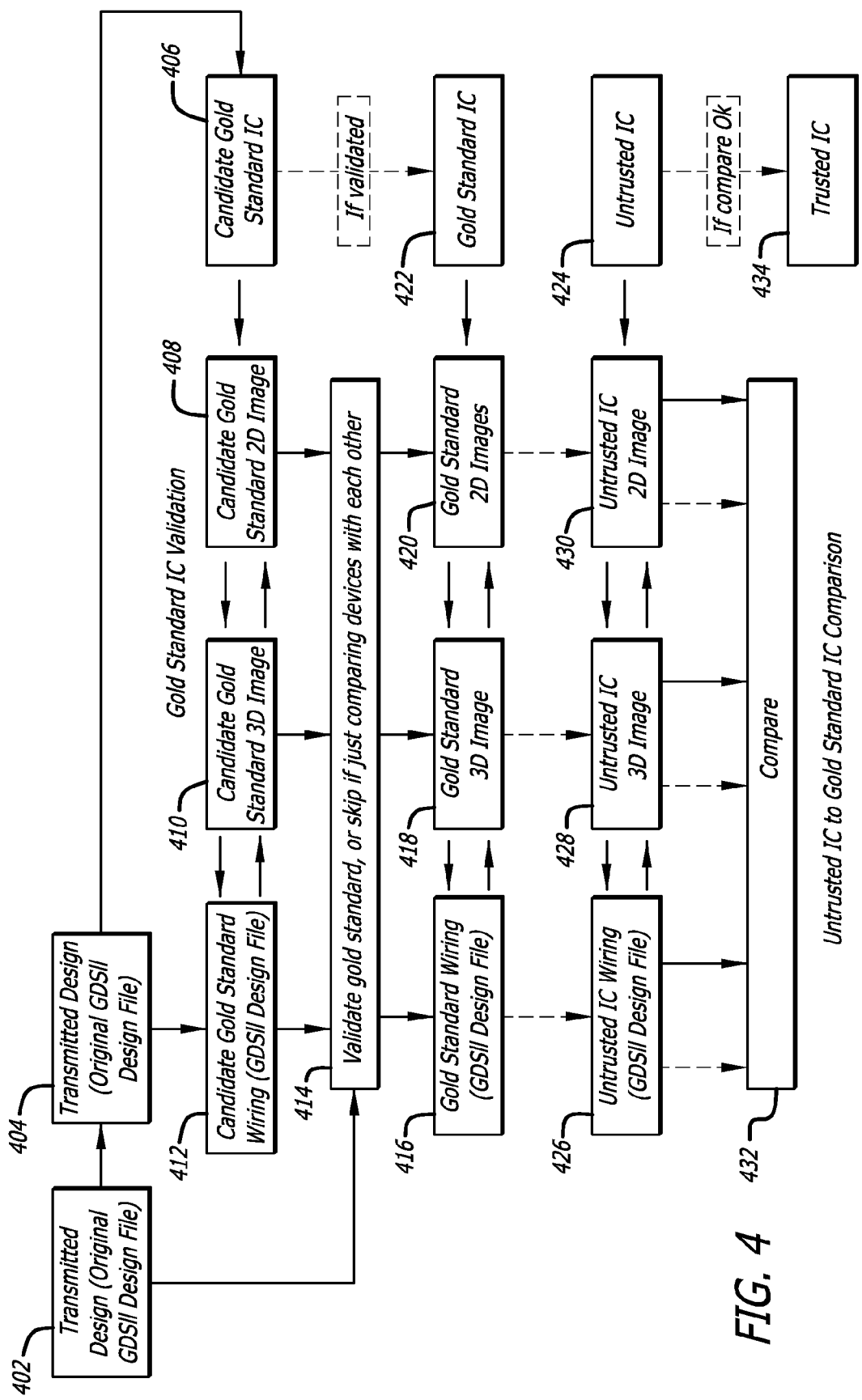
FIG. 4 illustrates an exemplary tool flow diagram of a method for IC validation using a "gold standard" reference design image according to the present disclosure.

An overall tool flow for hardware verification of integrated circuits using x-ray imaging according to an embodiment is shown in FIG. 4. First, an un-trusted foundry 404 manufactures ICs based on an original trusted GDSII design file 402 and returns them for inspection. The foundry may or may not make modifications to the original design, such as metal fill layers, and may or may not provide documentation of these modifications in the form of a modified design file. Alternately, devices may simply be procured from an un-trusted supply chain.

Next, to establish a "gold standard" reference article, an initial IC device 406 may be scanned with one or more 2D x-ray images (408). If enough 2D images of the device are made, tomographic reconstruction can be used to produce a detailed 3D representation 410 of the device's wiring interconnect. This 3D representation can then be converted into a recovered GDSII design file 412, representing the metal layers of the initial candidate "gold standard" device. In other embodiments, a design reference of a type or form other than a "gold standard" may be used.

To verify the device to be tested as a gold standard, one or more of these representations is compared against the original design file. If input from the foundry is provided, it can be used to enhance the validation process, i.e. recognizing features in the IC device, but the design from the foundry too is validated for consistency against the original design file. In terms of evaluation metrics, any differences discovered can be mapped back to the original design file and the affected transistors.

Once a gold standard device has been validated 414, its representations can be used to inspect additional ICs using a similar tool flow. If a gold standard device is provided externally, the validation step 414 can simply be skipped. Different approaches can be taken to imaging and making comparisons between ICs, and between ICs and reference design files.

Examples of different ways to make the same comparison are to compare full 3D datasets; to compare individual 2D images; or to convert a reference design into a 3D volume dataset, and then render it as a 2D image, and then compare this image with one seen from the x-ray microscope. Thus, 2D images 420 and 3D images 418 of a validated gold standard IC 422 may be derived from gold standard design file 416. Similarly, from an un-trusted IC 424 based on un-trusted design file 426, 2D images 430 and 3D images 428 may be taken. Comparison step 432 may determine whether additional or modified structures are present in the un-trusted IC that are not present in the gold standard design. If no such structures are identified, the result is a determination of a trusted IC 434.

The tool flow for IC inspection may advantageously benefit from advancements which have been made in the field of medical imaging. Many of the latest research tools and methods are available in open-source form, such as the Image Segmentation and Registration (ITK) Toolkit, sponsored by NIH, GE Research, Kitware, and several universities; Paraview (a package for visualizing exceptionally large 2D and 3D datasets), sponsored by Los Alamos, Sandia and Lawrence Livermore National Laboratories, the Army Research Laboratory, Kitware, etc.; and the Visualization Toolkit (VTK) also developed and used by many of the same organizations. These exemplary tools and others may be tailored to the IC inspection problem to convert and compare GDSII, and 3D volume datasets and to accurately register images generated by the x-ray microscope.

Wiring Dimensions

Figure 5:
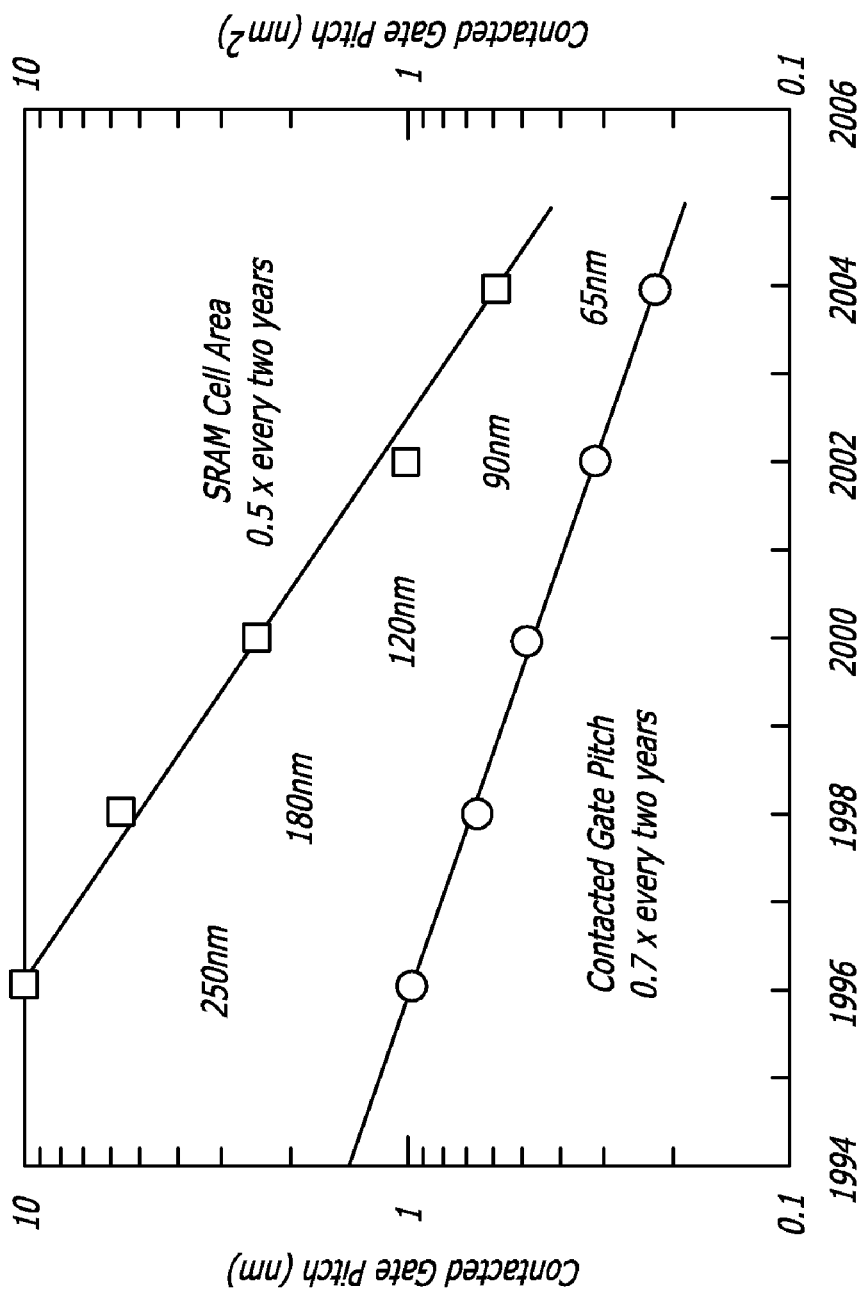
FIG. 5 shows a graph showing wiring scaling trends contacted for an SRAM cell from a period of 1994 to 2006.
Figure 6:
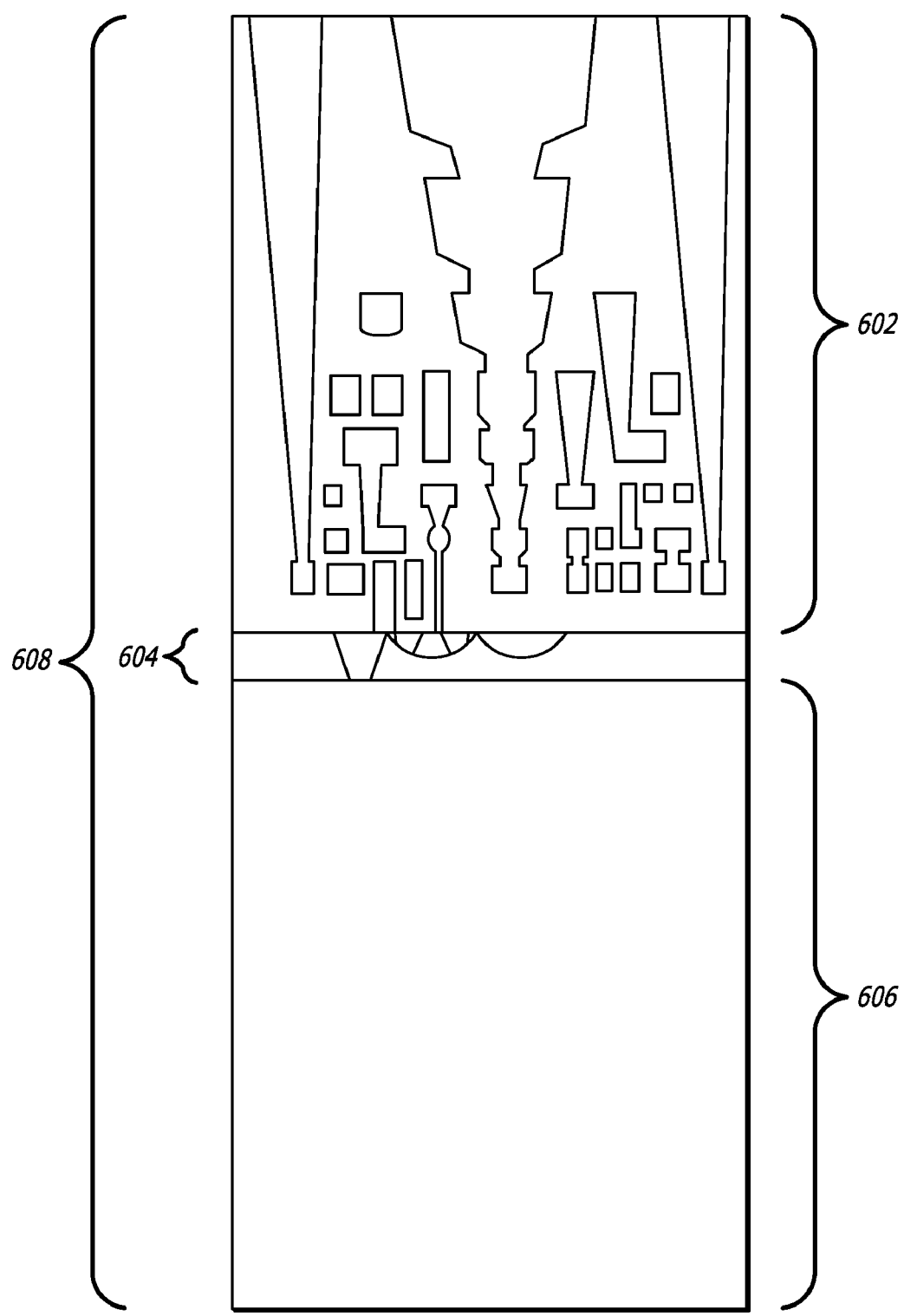
FIG. 6 illustrates a microscopic cross-sectional image of a semiconductor device using the Intel 65 nm technology.

The technologies disclosed herein are capable of inspecting complete ICs having current and future wiring dimensions. Table 1 shows the wiring dimensions for an Intel 65 nm technology, a current IC technology. FIG. 5 shows a graph showing wiring scaling trends contacted for an SRAM cell from a period of 1994 to 2006. FIG. 6 illustrates a microscopic cross-sectional image of a semiconductor device using the Intel 65 nm technology.

TABLE 1

Layer pitch, thickness and aspect ratio

| Layer | Pitch (nm) | Thick (nm) | Aspect Ratio |
|---|---|---|---|
| Isolation | 220 | 320 | — |
| Polysilicon | 220 | 90 | — |
| Contacted gate pitch | 220 | — | — |
| Metal 1 | 210 | 170 | 1.6 |
| Metal 2 | 210 | 190 | 1.8 |
| Metal 3 | 220 | 200 | 1.8 |
| Metal 4 | 280 | 250 | 1.8 |
| Metal 5 | 330 | 300 | 1.8 |
| Metal 6 | 480 | 430 | 1.8 |
| Metal 7 | 720 | 650 | 1.8 |
| Metal 8 | 1080 | 975 | 1.8 |

Referring to FIG. 6, overall wafer thickness 608 is approximately 800 um during manufacturing, with the top ~10 microns 602 devoted to layers of metal wiring interconnect. Wafers are routinely thinned to less than 100 um after manufacturing for stacked die packaging. The smallest dimensions of the metal 1 layer are currently well over 100 nm, and are not predicted to be significantly less than 100 nm for several IC process generations. (By contrast, the diffusion layer 604 of semiconductor doped regions may be less than one micron.) Current leading edge manufacturing processes have up to 12 metal layers. Accurately imaging this depth and complexity of metal interconnect is well within the capabilities of the unique x-ray microscope systems described below.

X-Ray Microscopic Capabilities

Figure 7B:
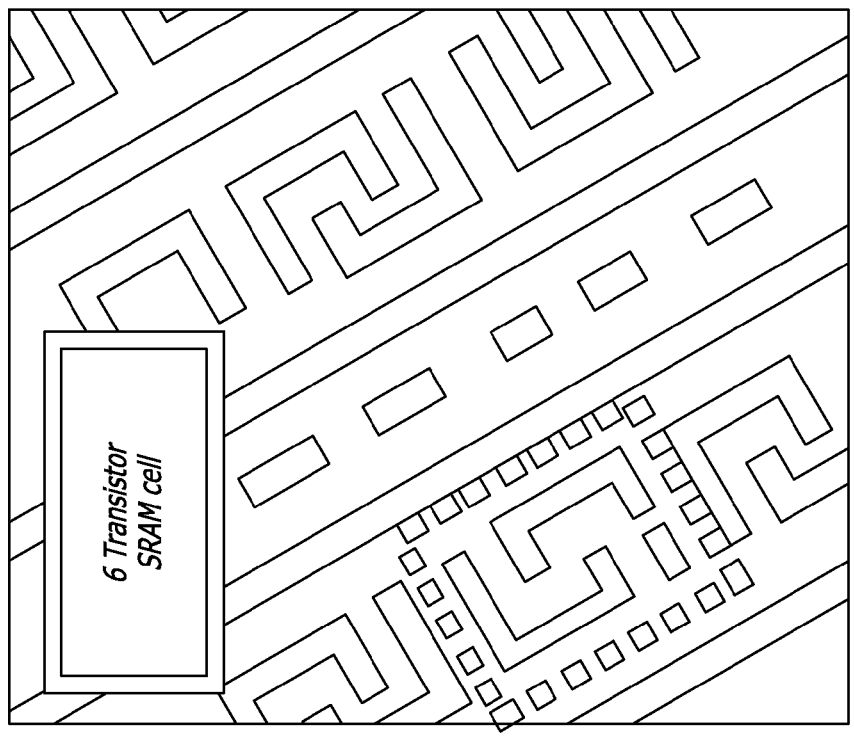
FIG. 7B illustrates a two-dimensional microscopic image of a six-transistor SRAM cell on one of the metal layers of the 90 nm Intel P4 processor.
Figure 7A:
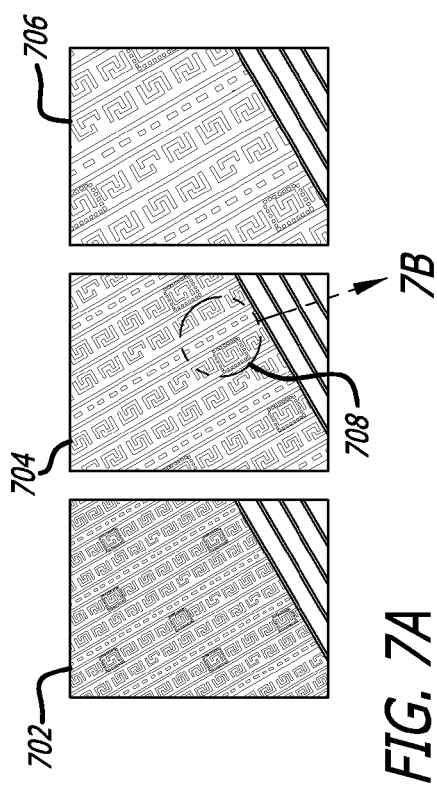
FIG. 7A illustrates a microscopic image of three of nine Cu metallization layers of the nine metal layers of a 120 nm Intel P4 processor.

X-ray microscopy has been shown to be a leading candidate technology for IC verification because it has demonstrated capabilities such as non-destructive and precise imaging of the entire stack of metal wiring layers in ICs manufactured from technologies down to 65 nm. The imaging of three of the nine layers 702, 704, and 706 from a 120 nm Intel P4 processor is shown in FIG. 7A. The Cu structures went down to 90 nm. The image was derived from a virtual de-layering of nine Cu metallization layers (with only three shown for clarity) using non-destructive x-ray tomography. A zoomed portion 708 was imaged as FIG. 7B, which shows a six-transistor SRAM cell. FIG. 7B is an illustration of a single raw two-dimensional image at normal incidence before any tomography is applied.

Computed Tomography

Computed tomography is the process by which a higher order representation of an object is created from a series of lower-order projections of that same object. For example, a 3D representation of a particular object can be created from a series of 2D images of that object collected from a sufficient number of viewing angles. First a series of projected 2D views of the area shown may be taken from a large number of angles. Next these images may be combined using computed tomography algorithms to produce a 3D density representation. Fortunately, since the imaging optics of the x-ray microscope are at such a small angle, the mathematics for tomographic reconstruction can be greatly simplified by assuming a parallel projection hypothesis. Once the 3D density representation is computed, it can be "sliced" into the series of 2D images, or layers which are shown, for example, in FIG. 7A.

X-Ray Imaging Device

In an aspect, the IC verification technique described herein may use an x-ray imaging device for producing one or more base images of a trusted or un-trusted IC for comparison purposes. An x-ray imaging device includes any device that uses x-rays to form an image of a sample. X-ray imaging techniques include, by way of example, x-ray microscopy and diffraction imaging. In one embodiment, an x-ray microscope is used to produce images of the IC. The x-ray microscope uses a condenser, a zone plate objective lens, and an x-ray source to send x-rays through an IC to produce an image.

Figure 8:
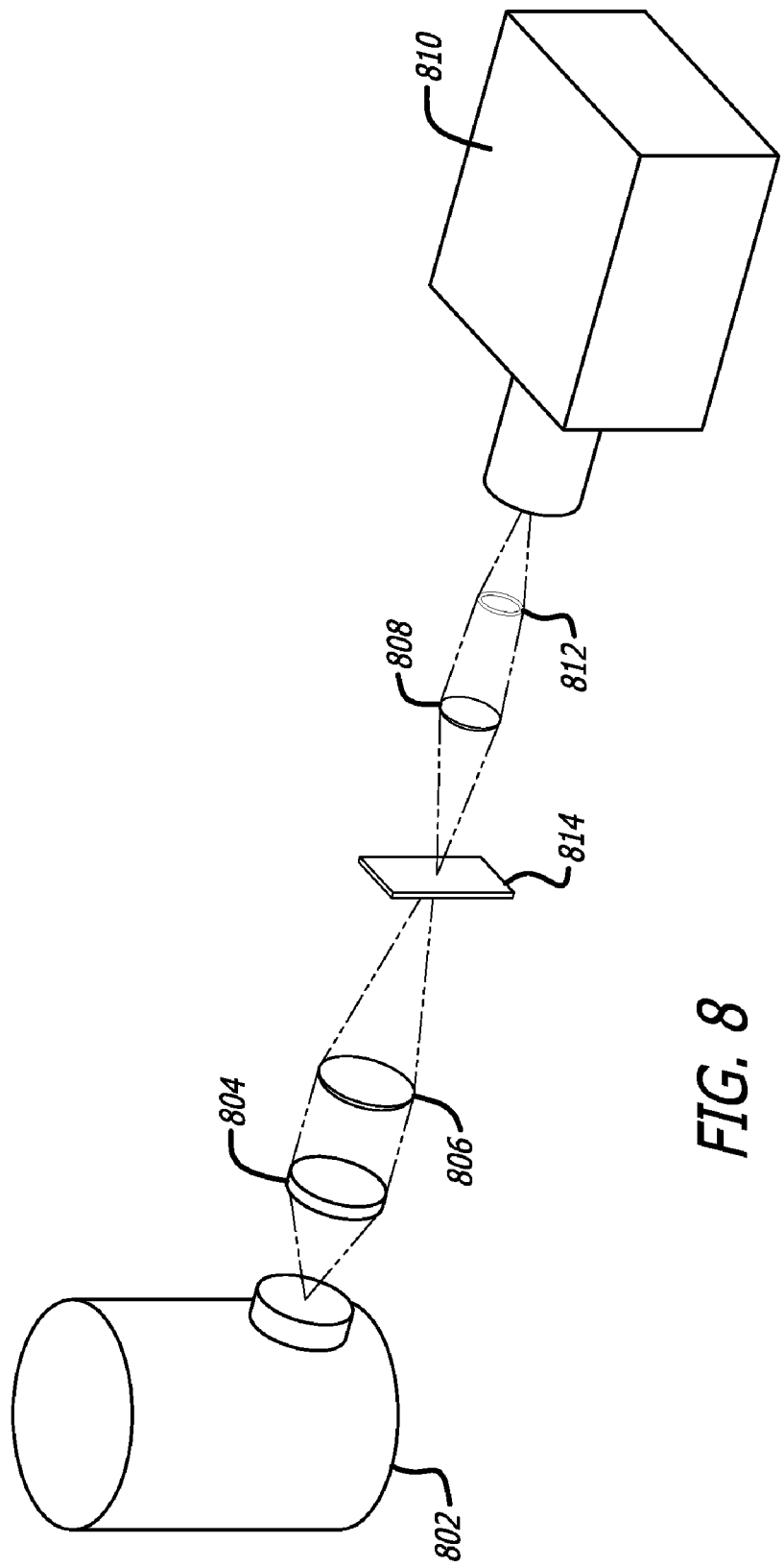
FIG. 8 illustrates a conceptual diagram of the main components of an x-ray microscope for verifying integrated circuits according to an aspect of the present disclosure.

FIG. 8 shows a conceptual diagram of the main components of an x-ray microscope for verifying an integrated circuit sample 814 according to an embodiment. X-rays may be obtained, for example, from either a laboratory source 802 or a synchrotron source. The optical elements may comprise circular diffraction gratings, such as Fresnel zone plates 808, followed by a high-resolution CCD imager 810. An energy filter 804 and condenser lens reside between the x-ray source and the sample 814. Between the zone plate 808 and the CCD imager/detector 810 lies phase ring 812.

Figure 9:
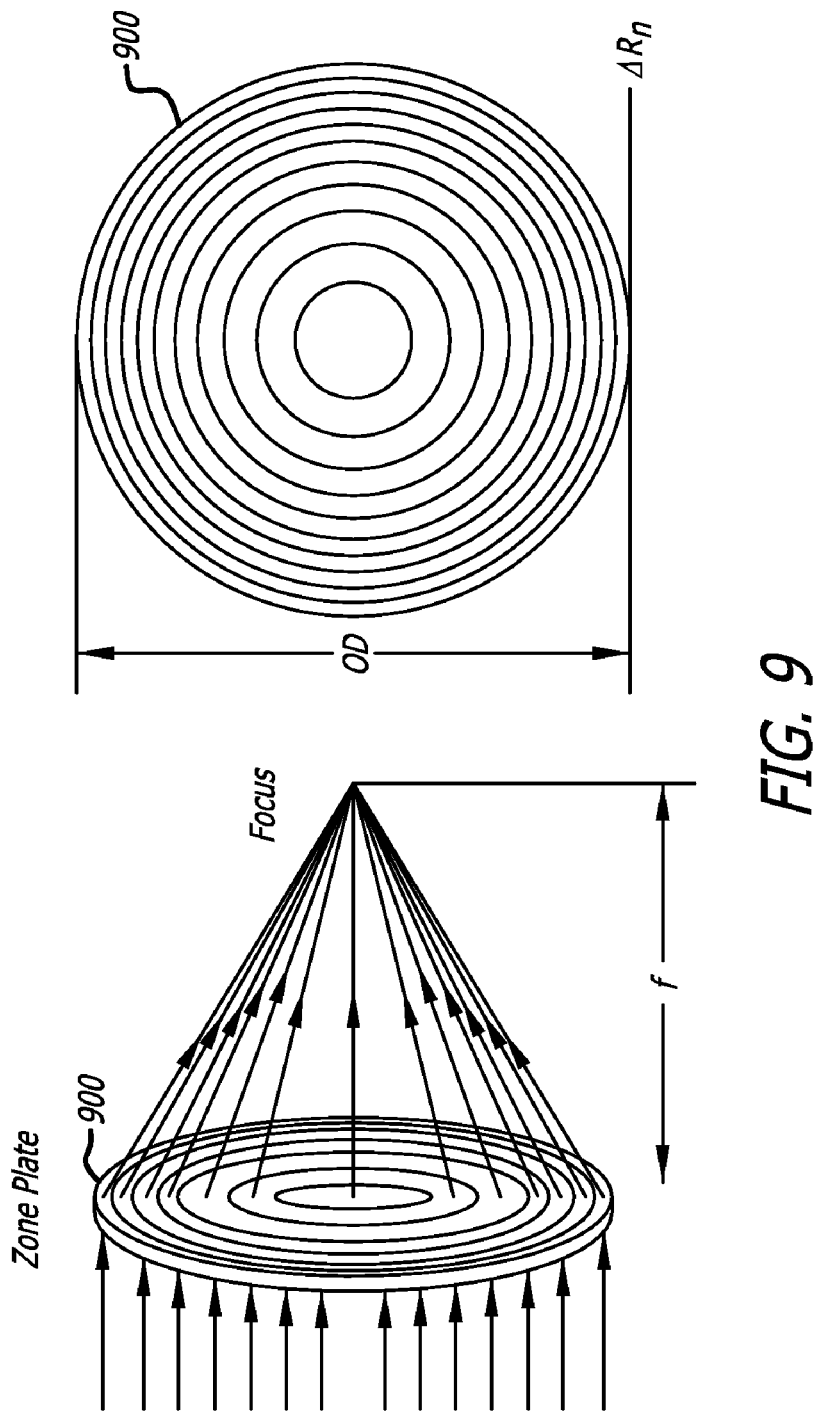
FIG. 9 illustrates side and front views of a fresnel zone plate used in an embodiment of an x-ray microscope for verifying integrated circuits according to an aspect of the present disclosure.

An important technology in building x-ray microscopes capable of imaging ICs is the design and manufacture of zone plates capable of focusing hard x-rays. Zone plates are diffractive x-ray lenses having high resolution (e.g., <30 nm). A circular grating with a varying radial pitch focuses x-rays to a point P, as shown in FIG. 9. The principal metrics of zone plates are defined by their aspect ratio which affects their efficiency and ability to focus hard x-rays and their spatial imaging resolution. The value f is the focal length. $\Delta R_n$ represents the varying radial pitch of the circular grating 900. The focal length f has a strong wavelength $\lambda$ dependence as is apparent from the following relationship:

$$f = \frac{OD\Delta R_n}{\lambda} \quad (1)$$

Figure 10:
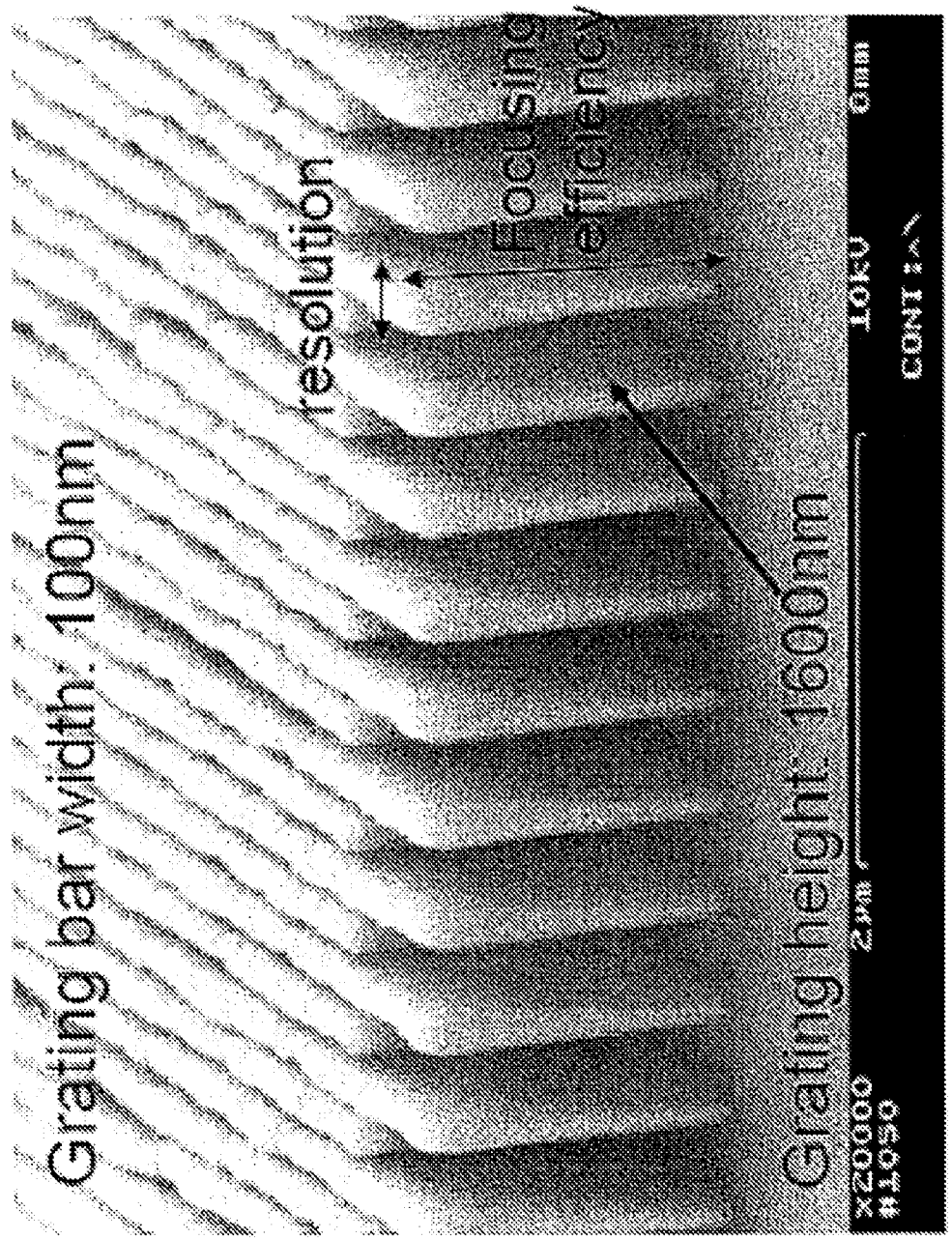
FIG. 10 illustrates a magnified view of the grating bars of gold zone plates of an x-ray microscope. The view is approximately a 20,000 times magnification.

Thus, the use of zone plates enables wavelength specific imaging. FIG. 10 illustrates a magnified view of the grating bars of gold zone plates of an x-ray microscope. The view is approximately a 20,000 times magnification. The grating height, which is proportionate to the focusing efficiency, in one embodiment is approximately 1600 nm. The grating bar width, proportionate to the resolution, in this embodiment is approximately 100 nm. The zone plates, like the gold ones in the embodiment of FIG. 10 may be fabricated out of a high-Z material using electron beam lithography, reactive ion etching, and electroplating.

A second innovation in the microscope design described herein is the use of a Zernike phase contrast mode. The contrast mode enables imaging of the difference in phase caused by x-ray diffraction of a specimen as opposed to simple attenuation. This differencing operation enhances the sensitivity of the microscopy considerably allowing inspection of deep and fine-scale structures which could not be seen otherwise. The unprecedented results that have been demonstrated by this microscope are due also in part to the optimization of this contract mode to specifically enhance differences between Si and Cu structures.

Figure 11:
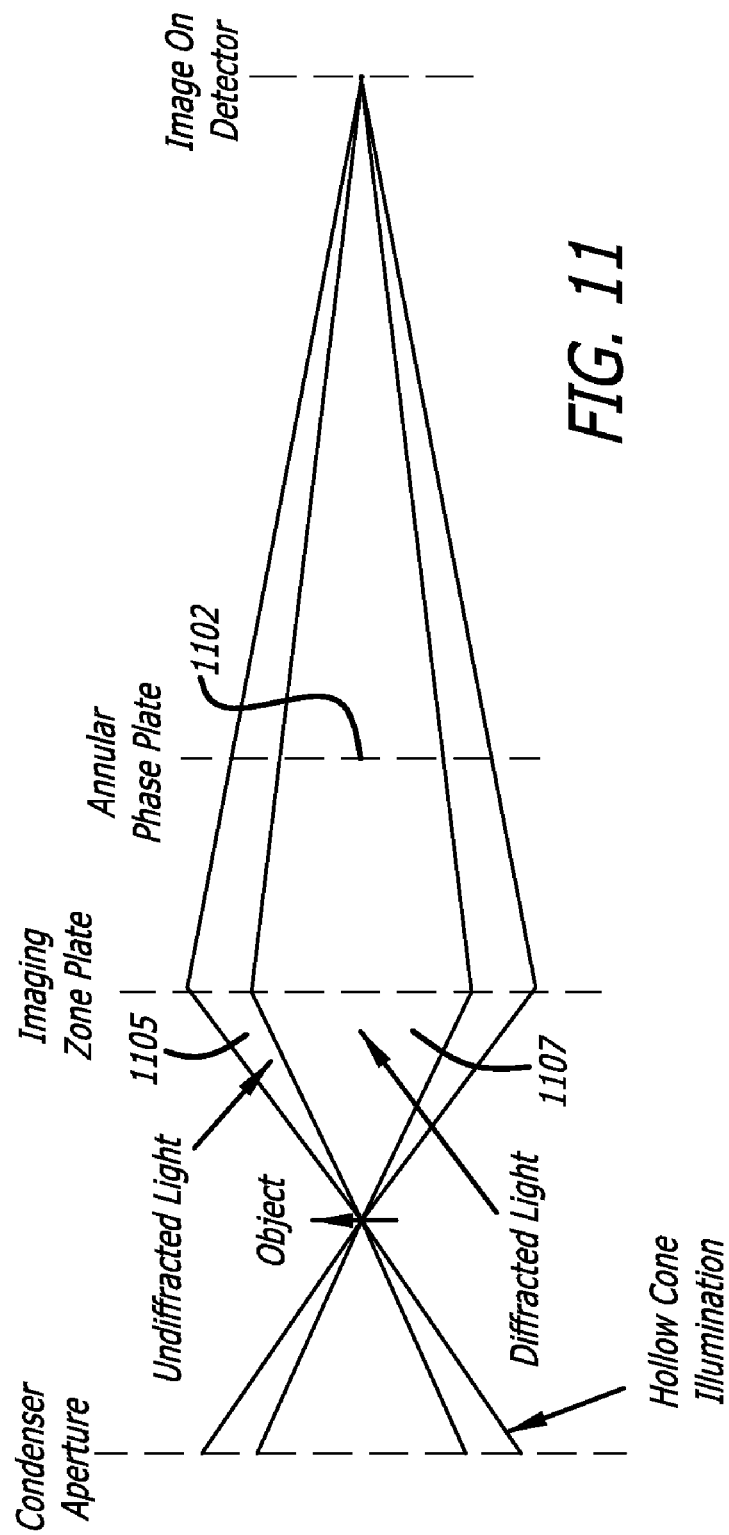
FIG. 11 illustrates a conceptual diagram of an x-ray microscope using an annular phase plate according to an aspect of the present disclosure.
Figure 12:
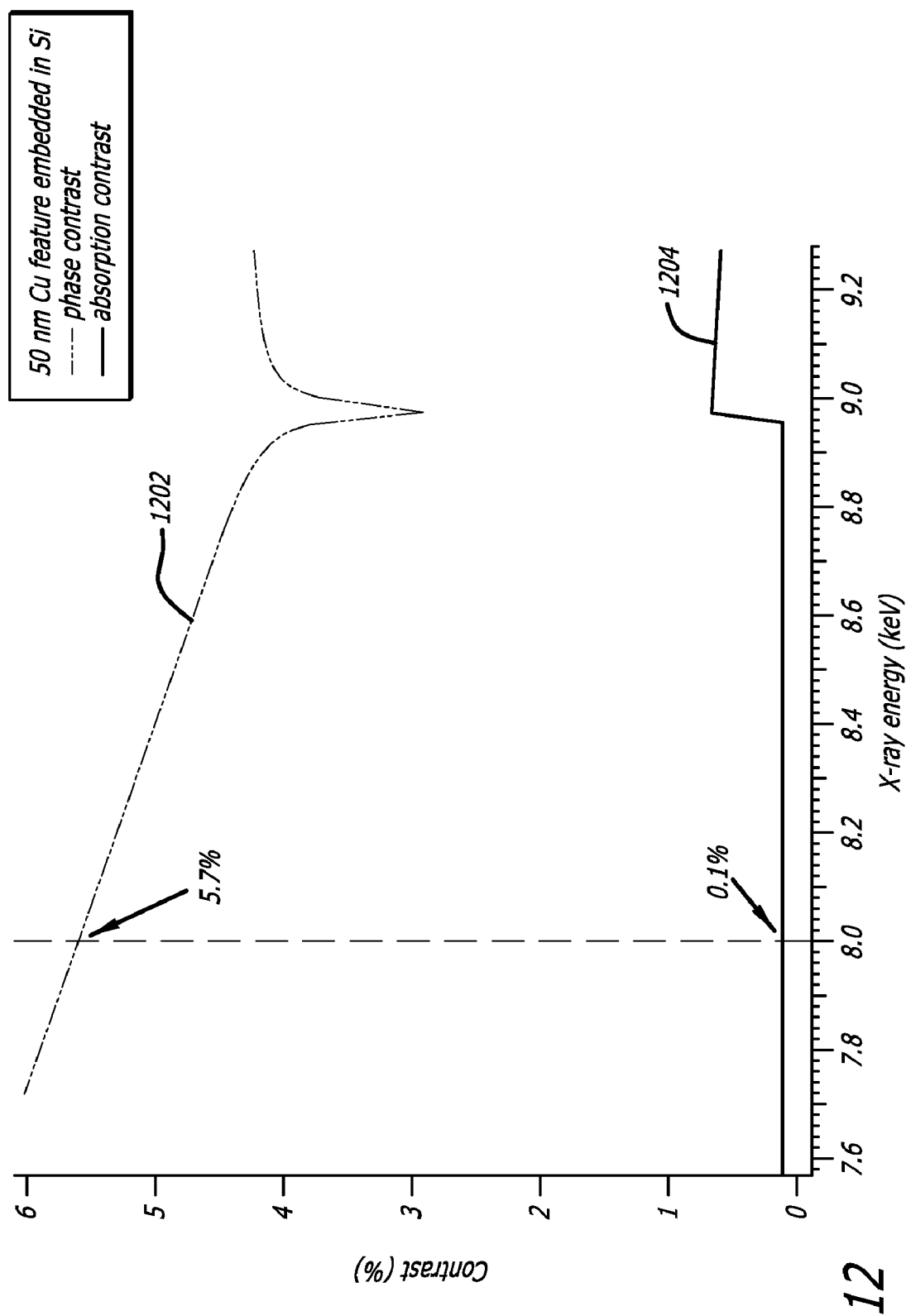
FIG. 12 illustrates a exemplary graph comparing image contrast boost using Zernike phase contrast versus absorption contrast.

FIG. 11 illustrates a conceptual diagram of an x-ray microscope using an annular phase plate 1102. Phase plate 1102 shifts undiffracted light 1105 by $3\pi/2$ for a negative phase contrast. Diffracted light 1107 interferes with undiffracted light 1105 and phase structure transfers to intensity variation (i.e., absorption suppressed). FIG. 12 illustrates a exemplary graph comparing image contrast boost using Zernike phase contrast versus absorption contrast. Image contrast K can be defined by the relationship $$k = \frac{I_1 - I_2}{I_1 + I_2} \quad (2)$$

The graph is directed to a 50 nm Cu feature embedded in silicon, and shows a phase contrast curve 1202 and an absorption contrast curve 1204. The contrast percentage for curve 1202 is 5.7%, while the contrast percentage for curve 1204 is 0.1%. As can be seen, the phase contrast in this example is enhanced by a factor greater than 50. This enhancement is critical for the visualization of small features using hard x-rays.

Accordingly, computed tomography may be used to visualize defects buried inside the interconnect layers of an IC, without de-layering the IC as is conventionally performed.

It is a current limitation of the approach that bright light sources such as a synchrotron are needed to generate images in reasonable periods of time. While building a synchrotron facility dedicated to the inspection of ICs may be expensive, the cost of such a solution must be weighed against the cost of building a next-generation secure foundry in a current technology. It is also expected that alternate technologies will be developed to generate x-rays.

To get the highest contrast available, and to facilitate working with a lab-scale x-ray source (8 keV), ICs may be thinned to less than 100 um so that there is sufficient penetration of x-rays through the sample. This is not a significant burden as it is commonplace to thin dies to dimensions less than this for multi-die packaging applications. If a synchrotron light source is used; as may be the case in the embodiment for production-line inspection, higher energies may be used which have more penetration power into silicon. While the contrast at these higher energy levels is not as great as at 8 keV, it is not significantly different either.

Radiation Effects

In an aspect, an annealing step is used to heat irradiated IC devices following exposure to x-rays in order to reduce the effect of any damage caused by the x-rays. Much or most of the damage caused to any of the ICs can be reversed through this annealing process. The inventors have concluded that x-ray imaging on devices having smaller form factors as discussed in this disclosure, coupled with an annealing step, when necessary, advantageously enables the IC verification process disclosed herein to be non-destructive.

Invisible Transistors and Barrier Circuits

A central tenet of verification of IC manufacturing by x-ray imaging is that the coupling of a functional design test, which exercises all the functionality of the expected circuits in an IC, with a detailed physical wiring inspection tightly constrains the types of modifications which can be made to a design and evade detection. While it may possible to create additional transistors which are nearly invisible to x-rays, e.g. diffusion and poly structures which are mostly Si, making these transistors functional in the design by cascading them into gate structures where the output of one transistor functions as the "gate" of another, requires the use of additional metal structures which would be detected. Therefore if significant additional functionality is added, it must take away from, or share, functionality with existing structures that are already well-tested. This circular logic is the basis for x-ray inspection.

Image Processing Components

Figure 13:
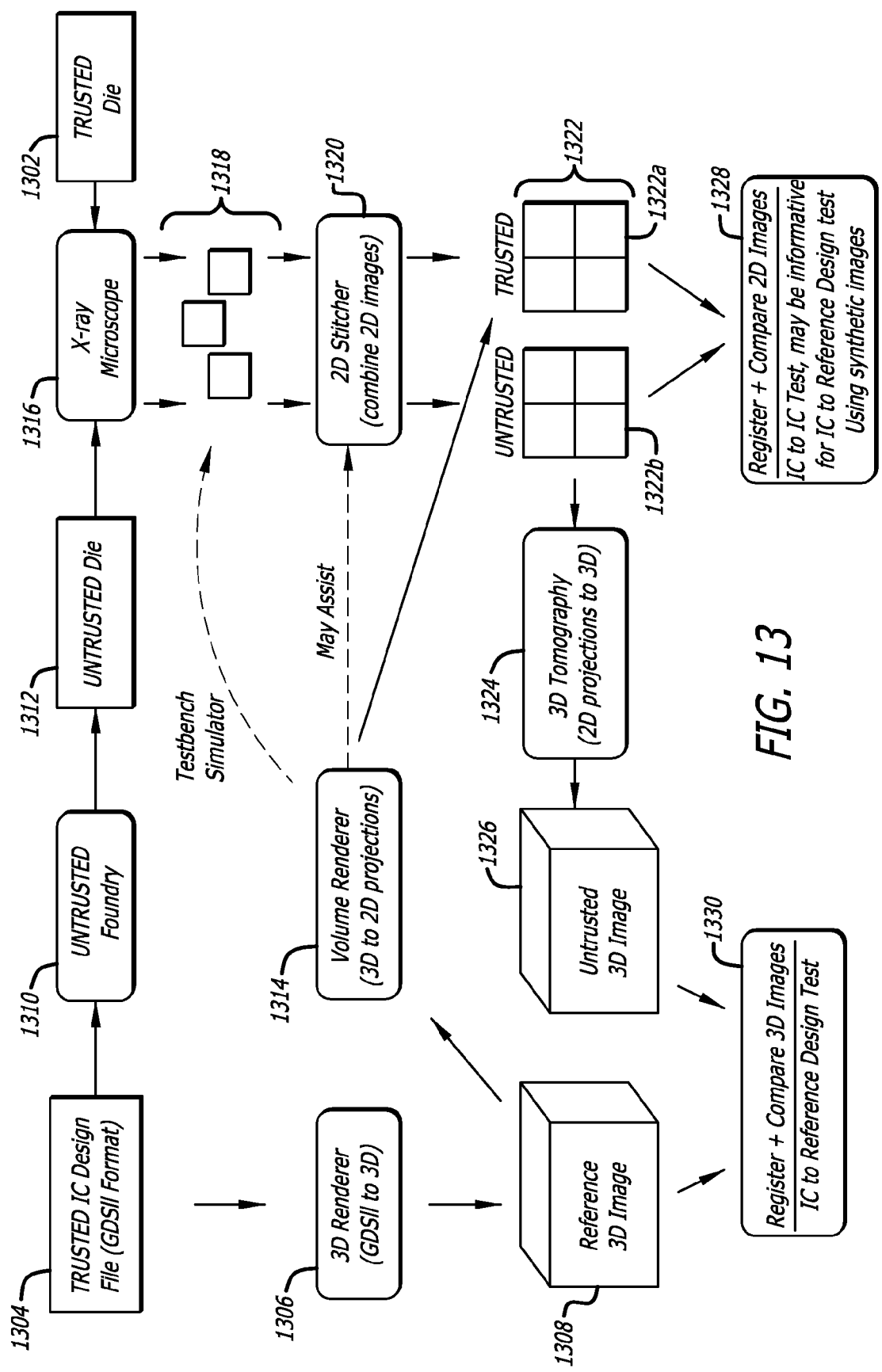
FIG. 13 illustrates a flow diagram for IC verification in accordance with the present disclosure.

FIG. 13 illustrates a flow diagram for IC verification in accordance with the present disclosure. A hardware supplier may produce a trusted IC design file, for example, in a GDSII, OASIS, or other known format (1304). The design file 1304, along with layer mapping, layer thickness and layer density information, may be submitted to a 3D rendering engine 1306 to generate an output volume dataset comprising a reference 3D image 1308. In one embodiment, this 3D rendering step is performed by converting the GDSII "boundary" and "path" elements to 2D images and then stacking the sheets of 2D images to form the 3D volume. The trusted IC design file 1304 may be submitted to the un-trusted foundry 1310. The foundry thereupon fabricates the un-trusted die 1312. In one embodiment, the design file may be used as described below to generate one or more 2D or 3D reference images of part or all of an IC having the physical properties and connected components described in the design file. The reference image (s) may thereupon be compared with one or more images of a part or all of an un-trusted IC device to determine whether unauthorized circuit insertions or modifications are present in the un-trusted device.

In another embodiment, the reference image may be generated from a trusted IC, such as, for example in the case where a commercial entity is seeking to verify the integrity of a shipment of additional ICs having an identical part number to the trusted IC. In this embodiment, the reference image is derived from the trusted IC directly instead of the design file.

In one embodiment where one or more 2D reference images are compared with one or more 2D entrusted images (step 1428, the reference 3D image 1308 may be submitted to volume renderer engine 1314 which converts the 3D volume to 2D synthetic microscope images 1422a. The input to volume renderer 1314 includes the 3D volume dataset at the desired viewing pose. In one embodiment, open source 3D rendering software is used. Alternatively, the 2D images 1422a may be generated directly via 3D resampling and rotation and summing (i.e., parallel projection techniques).

X-ray microscope 1316 may then be applied to un-trusted die 1312 and trusted die 1302 to obtain a matrix of 2D microscope images 1318. A 2D stitcher 1320 may then be used to assemble large 2D images from the matrices of smaller images. The 2D images may be either actually obtained from x-ray microscope 1316, or alternatively synthetically obtained from volume renderer 1314. Image position and microscope calibration data may also be received by the 2D stitcher from the microscope 1316 and/or volume renderer 1314. The output to the 2D stitcher 1320 may include a combined mosaic image 1322 of the matrices of 2D images 1318 which includes the full IC—a mosaic image 1322a for the trusted die and a mosaic image 1322b for the un-trusted die. In one embodiment, an algorithm used for the 2D stitcher is as follows: the 2D images 1318 are normalized to account for microscope geometric and intensity distortion. A gradient descent is used to compute the maxima of normalized correlation pairwise between images over a region. Multiple starting points may be seeded and local maxima saved. A global maximum correlation over the mosaic image may thereupon be computed over the mosaic image 1322 using pairwise correlations. In one embodiment, the 2D stitcher may be generated based on an open source medical imaging software library which provides registration and deformation algorithms as primitive operations.

In other embodiments where single 2D microscope images 1318 are being compared with 2D reference images and no combining of 2D images is necessary, the 2D stitcher shown in FIG. 13 may simply comprise instructions or code for appropriately calibrating one or more the images 1318 or converting the images 1318 to a format suitable for use in the comparison process 1328 or 1330.

Thereupon, 3D tomography 1324 may be applied to the un-trusted mosaic image 1322b to compute an un-trusted 3D image 1326. Here, 2D composite images 1322b from multiple viewing angles (e.g., up to)140° may be used as inputs to produce the 3D volume dataset. In one embodiment, for the 3D tomography, a filtered back-projection is used. More specifically, the two dimensional Fourier transform of each 2D image 1322b may be computed. Each transformation may then be "back projected" into the sampled 3D volume. In this embodiment, the tomography processing may be simplified due to the use of parallel projection of microscope image.

The trusted 2D images 1322a and un-trusted 2D images 1322b of the trusted and un-trusted ICs, respectively, may be registered and compared in an IC-to-IC test 1328. The IC-to-IC comparison may be based on x-ray views. Alternatively, the un-trusted IC may be compared to a synthetic view of the trusted GDSII design using the volume renderer 1314. In another alternative a partial IC-to-IC comparison may be performed, and the verification may be completed using the GDSII reference design. In the comparison step 1328, the 2D mosaic images 1322a and 1322b taken from the same viewing angle are compared, and the output may comprise a dataset including image areas which exceed a predetermined threshold. In one embodiment, the algorithm used in the comparison engine 1328 may be similar to the 2D stitcher. In particular, a gradient descent may be used to find the best-fit between the two images. Then differences may be flagged where the image exceeds the threshold.

In addition, the reference 3D image 1308 may be compared with the un-trusted 3D image 1326 in an IC to Reference Design test 1330. The output of this comparison may include local differences and thresholds for connected components included in the real data set 1326 but not in the synthetic data set 1308. An algorithm according to an embodiment for the comparison engine 1330 includes registering the 3D datasets, using 3D segmentation to identify connected components and medial axes in synthetic and real datasets, performing a one-to-one matching between connected components in each dataset and matching medial axes, and identifying unconnected and shorted segments and segments whose medial axes are substantially different.

Software toolkits and applications which may be used to implement the engines in FIG. 13 include, for example, Image Segmentation and Registration (ITK), Visualization (VTK), and Massive dataset visualization (Paraview).

Figure 14:
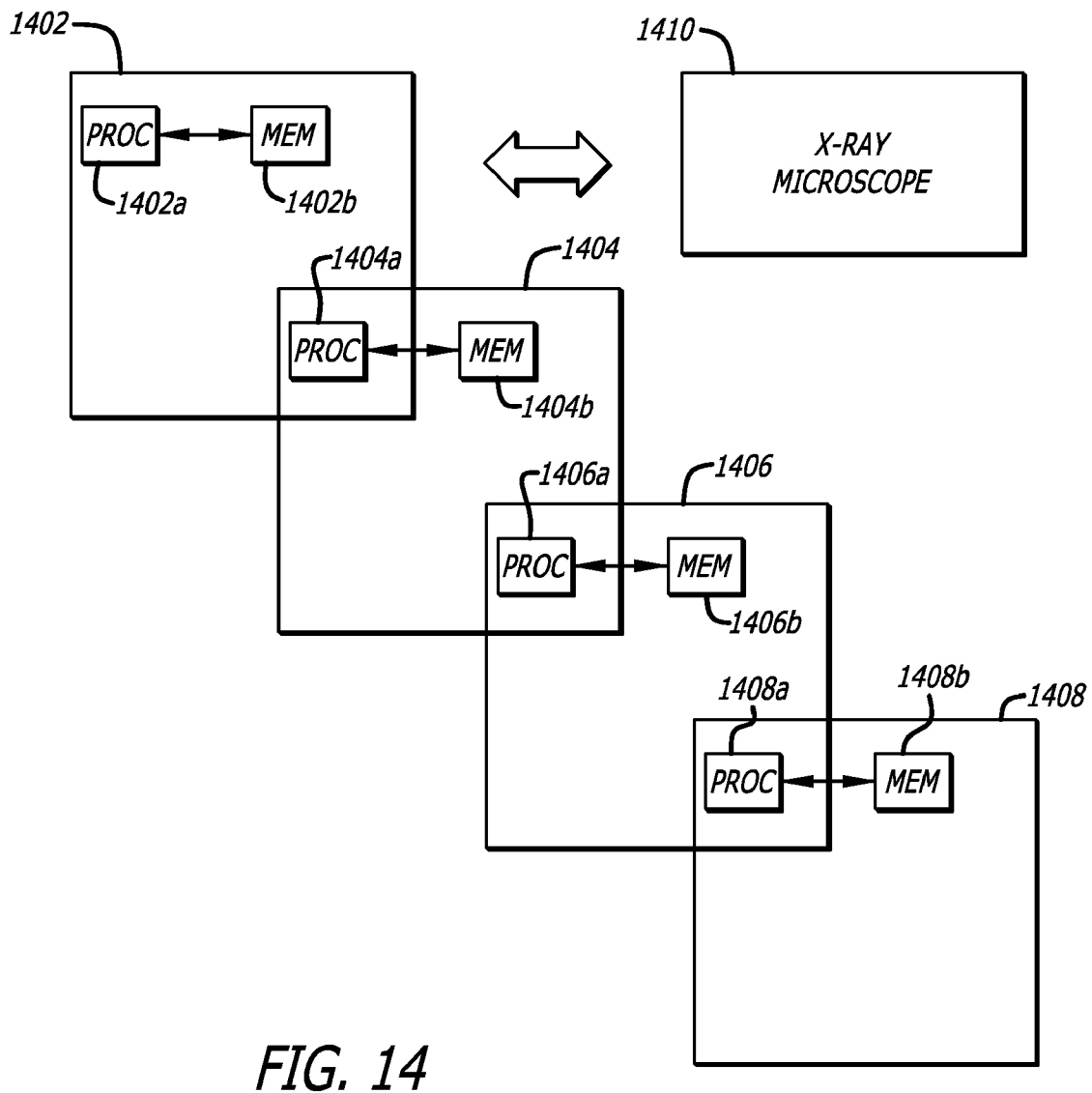
FIG. 14 illustrates a set of four computing machines and an x-ray microscope for performing a verification technique according to the present disclosure.

Each of the rendering engines in FIG. 13 may be implemented via a processor or a processing system, as shown in FIG. 14. FIG. 14 shows four computing machines 1402, 1404, 1406, and 1408 that are part of a computing system. The computing machines are separate in this example, however this need not be the case. The functional relationship of the machines is demonstrated by the overlapping boxes representing computing machines 1402, 1404, 1406, and 1408. In this example, computing machine 1402 is coupled to the x-ray microscope 1410.

In general, the processing system 1402a, 1404a, 1406a, 1408a may be implemented using hardware, software, or a combination of both. By way of example, a processing system may be implemented with one or more integrated circuits (IC). An IC may comprise a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. A general purpose processor may be a microprocessor, but in the alternative, the general purpose processor may be any conventional processor, controller, microcontroller, or state machine. A processing system may also be implemented as a combination of computing devices, e.g., a combination of a DSP and a microprocessor, a plurality of microprocessors, one or more microprocessors in conjunction with a DSP core, or any other such configuration.

A memory system ("memory") 1402b, 1404b, 1406b, or 1408b may be coupled to the processing system. The memory system may include RAM, ROM, flash memory, or any known type of memory module or integrated circuit in whatever form. Alternatively or additionally, the memory unit may include storage include one or more hard drives, optical drives, tape drives, or other storage. The memory may collectively hold and store information for use by the processing unit as described in this disclosure, including for example, computer programs, learned acoustic signatures, and the like.

The term "computing system" as described herein may refer to a single computing machine or to multiple computing machines, coupled together through a hardwired connection, through a network, or otherwise.

The code or instructions may be embodied in one or more machine-readable media to support software applications. Software shall be construed broadly to mean instructions, programs, code, or any other electronic media content whether referred to as software, firmware, middleware, microcode, hardware description language, or otherwise. Machine-readable media may include storage integrated with a processor, such as might be the case with an ASIC. Machine-readable media may also include storage external to a processor, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. In addition, machine-readable media may include a transmission line or a carrier wave that encodes a data signal. Those skilled in the art will recognize how best to implement the described functionality for the processing system. Moreover, in some aspects any suitable computer-program product may comprise a computer-readable medium or machine-readable medium comprising codes relating to one or more of the aspects of the disclosure. In some aspects a computer program product may comprise packaging materials.

The various components that have been discussed may be made from combinations of hardware and/or software, including operating systems and software application programs that are configured to implement the various functions that have been ascribed to these components above and in the claims below. The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

The phrase "means for" when used in a claim embraces the corresponding structures and materials that have been described and their equivalents. Similarly, the phrase "step for" when used in a claim embraces the corresponding acts that have been described and their equivalents. The absence of these phrases means that the claim is not limited to any of the corresponding structures, materials, or acts or to their equivalents.

Nothing that has been stated or illustrated is intended to cause a dedication of any component, step, feature, object, benefit, advantage, or equivalent to the public, regardless of whether it is recited in the claims.

In short, the scope of protection is limited solely by the claims that now follow. That scope is intended to be as broad as is reasonably consistent with the language that is used in the claims and to encompass all structural and functional equivalents.

We claim:

1. A system for verifying the integrity of integrated circuits (ICs) procured from an un-trusted source, comprising:
   an x-ray imaging device; and
   a processing system configured to:
      cause said x-ray imaging device to generate one or more base images of an un-trusted IC;
      produce at least one un-trusted image using said one or more base images, said at least one un-trusted image comprising a plurality of connected components from said un-trusted IC;
      compare said at least one un-trusted image with at least one reference image comprising a plurality of connected elements from a trusted source; and
      identify one or more differences in said connected elements between said un-trusted image and said reference image.

2. The system of claim 1 wherein said un-trusted IC is fabricated from an un-trusted foundry pursuant to a design file provided to said foundry, and wherein said at least one reference image is generated based on said design file.

3. The system of claim 1 wherein said at least one reference image is generated based on one or more images of a trusted IC.

4. The system of claim 1 wherein said one or more base images comprise a plurality of sets of two-dimensional (2D) base images, wherein each said set of 2D base images is generated using a different viewing angle of said x-ray imaging device, and wherein said generating at least one un-trusted image further comprises:
   assembling, for each set of 2D base images, a composite 2D image by combining the 2D images in the set;
   producing said at least one un-trusted image as a three dimensional (3D) image based on said plurality of assembled composite 2D images.

5. The system of claim 1 wherein said producing at least one un-trusted image using said one or more base images comprises formatting said one or more base images to obtain said at least one un-trusted image.

6. The system of claim 1 wherein said x-ray imaging device comprises an x-ray microscope.

7. The system of claim 6 wherein an x-ray source of said x-ray microscope comprises a synchrotron.

8. The system of claim 1 wherein said un-trusted IC is annealed following exposure to said x-ray imaging device to reduce an effect of radiation damage.

9. The system of claim 1 wherein said design file comprises one of a GDSII design file and an OASIS design file.

10. The system of claim 1, wherein said producing said at least one un-trusted image comprises using 3D tomography.

11. A method for verifying the integrity of integrated circuits (ICs) procured from an un-trusted source by detecting unauthorized circuit insertions or modifications, comprising:
   generating, from an x-ray microscope, one or more base images of an un-trusted IC;
   producing at least one un-trusted image using said one or more base images, said at least one un-trusted image comprising a plurality of connected elements from said un-trusted IC;
   comparing said at least one un-trusted image with at least one reference image comprising a plurality of connected elements from a trusted source; and
   identifying one or more differences in said connected elements between said un-trusted image and said reference image using a processing system.

12. The method of claim 11 wherein said un-trusted IC is fabricated from an un-trusted foundry pursuant to a design file provided to said foundry, and wherein said at least one reference image is generated based on said design file.

13. The method of claim 11 wherein said at least one reference image is generated based on one or more images of a trusted IC.

14. The method of claim 11 wherein said one or more base images comprise a plurality of sets of two-dimensional (2D) base images, wherein each said set of 2D base images is generated using a different viewing angle of said x-ray imaging device, and wherein said generating at least one un-trusted image further comprises:

assembling, for each set of 2D base images, a composite 2D image by combining the 2D images in the set;

producing said at least one un-trusted image as a three dimensional (3D) image based on said plurality of assembled composite 2D images.

15. The method of claim 11 wherein said producing at least one un-trusted image using said one or more base images comprises formatting said one or more base images to obtain said at least one un-trusted image.

16. The method of claim 11 wherein an x-ray source of said x-ray microscope comprises a synchrotron.

17. The method of claim 11 wherein said un-trusted IC is annealed following exposure to said x-ray imaging device to reduce an effect of radiation damage.

18. The method of claim 11 wherein said design file comprises one of a GDSII design file and an OASIS design file.

19. The method of claim 11 wherein said producing said at least one un-trusted image comprises using 3D tomography.

20. A system for verifying the integrity of integrated circuits (ICs) procured from an un-trusted source, comprising:

x-ray microscope means for generating base images of an un-trusted IC;

stitching means for producing un-trusted images using said base images, said un-trusted images comprising a plurality of connected elements from said un-trusted IC;

comparison means for comparing said un-trusted images with a reference image comprising a plurality of connected elements from a trusted source; and determining means for identifying differences in said connected elements between said un-trusted images and said reference images.

21. The system of claim 20 wherein said un-trusted IC is fabricated from an un-trusted foundry pursuant to a design file provided to said foundry, and wherein said reference images are generated based on said design file.

22. The system of claim 20 wherein said reference images are generated based on one or more images of a trusted IC.

23. A system for verifying that an un-trusted integrated circuit is an accurate replica of a desired integrated circuit, comprising:

an x-ray imaging device; and a processing system configured to:

cause the x-ray imaging device to generate one or more images of connected elements within the un-trusted integrated circuit;

compare the one or more images, or information derived therefrom, with reference information indicative of connected elements within the desired integrated circuit; and identify one or more differences between the connected elements in the un-trusted integrated circuit and the connected elements in the desired integrated circuit based on the comparison.

* * * * *